(12) United States Patent
Nishihara et al.

(10) Patent No.: US 10,591,618 B2
(45) Date of Patent: Mar. 17, 2020

(54) X-RAY DETECTION DEVICE AND DETECTION METHOD

(71) Applicant: SONY CORPORATION, Tokyo (JP)

(72) Inventors: Toshiyuki Nishihara, Kanagawa (JP);
Kenichi Okumura, Tokyo (JP);
Tsutomu Imoto, Kanagawa (JP);
Masao Matsumura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/094,120

(22) PCT Filed: Apr. 7, 2017

(86) PCT No.: PCT/JP2017/014456
§ 371 (c)(1),
(2) Date: Oct. 16, 2018

(87) PCT Pub. No.: WO2017/183481
PCT Pub. Date: Oct. 26, 2017

(65) Prior Publication Data
US 2019/0094391 A1    Mar. 28, 2019

(30) Foreign Application Priority Data

Apr. 22, 2016  (JP) ................................. 2016-086217

(51) Int. Cl.
*G01T 1/16*    (2006.01)
*G01T 1/208*   (2006.01)
(Continued)

(52) U.S. Cl.
CPC .............. *G01T 1/208* (2013.01); *A61B 6/032* (2013.01); *A61B 6/5258* (2013.01); *G01T 1/2018* (2013.01); *A61B 6/4233* (2013.01)

(58) Field of Classification Search
CPC ........ G01T 1/20; G01T 1/2006; G01T 1/2018
See application file for complete search history.

(56) References Cited

U.S. PATENT DOCUMENTS

2001/0038707 A1* 11/2001 Ohara .................. A61B 6/4233
382/132
2002/0024606 A1*  2/2002 Yuki ................. H01L 27/14603
348/302
(Continued)

FOREIGN PATENT DOCUMENTS

CN          103876766 A     6/2014
DE       102012224258 A1    6/2014
(Continued)

OTHER PUBLICATIONS

International Search Report and Written Opinion of PCT Application No. PCT/JP2017/014456, dated Jun. 6, 2017, 06 pages of ISRWO.

*Primary Examiner* — David P Porta
*Assistant Examiner* — Mamadou Faye
(74) *Attorney, Agent, or Firm* — Chip Law Group

(57) ABSTRACT

The X-ray detection device according to an aspect of the present disclosure includes a scintillator that generates scintillation light in response to incident X-rays; a detection unit including a plurality of pixels each generating a pixel signal in response to the scintillation light incident thereon; and an output unit that generates X-ray two-dimensional projection data by using the pixel signals of the pixels. A pixel of the detection unit includes a plurality of subpixels that performs photoelectric conversion in response to the scintillation light; an AD conversion unit that applies AD conversion to outputs of the subpixels; and an adder that generates the pixel signal corresponding to the pixel by adding up outputs of the plurality of subpixels after the AD conversion. The present disclosure is applicable to an X-ray CT device and an X-ray FPD device.

12 Claims, 15 Drawing Sheets

(51) Int. Cl.
*A61B 6/03* (2006.01)
*A61B 6/00* (2006.01)
*G01T 1/20* (2006.01)

(56) References Cited

U.S. PATENT DOCUMENTS

| | | | |
|---|---|---|---|
| 2006/0056581 A1 | 3/2006 | Hoffman et al. | |
| 2012/0081589 A1* | 4/2012 | Nishihara | H04N 5/32 |
| | | | 348/308 |
| 2012/0305786 A1* | 12/2012 | Dierickx | G01J 1/44 |
| | | | 250/371 |
| 2014/0177795 A1 | 6/2014 | Spahn | |
| 2015/0296162 A1* | 10/2015 | Kurokawa | H04N 5/3741 |
| | | | 250/208.1 |
| 2016/0259067 A1* | 9/2016 | Morton | G01T 1/2018 |
| 2016/0349192 A1* | 12/2016 | Yamakawa | A61B 6/02 |

FOREIGN PATENT DOCUMENTS

| | | |
|---|---|---|
| JP | 2003-202303 A | 7/2003 |
| JP | 2009-018154 A | 1/2009 |
| JP | 2014-121607 A | 7/2014 |

\* cited by examiner

FIG. 9
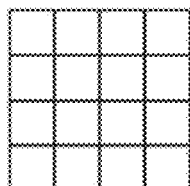
FIG. 10
BODY AXIS DIRECTION

X-RAY DETECTION DEVICE AND DETECTION METHOD

CROSS REFERENCE TO RELATED APPLICATIONS

This application is a U.S. National Phase of International Patent Application No. PCT/JP2017/014456 filed on Apr. 7, 2017, which claims priority benefit of Japanese Patent Application No. JP 2016-086217 filed in the Japan Patent Office on Apr. 22, 2016. Each of the above-referenced applications is hereby incorporated herein by reference in its entirety.

TECHNICAL FIELD

The present disclosure relates to an X-ray detection device and a detection method, and particularly relates to, for example, an X-ray detection device and a detection method, which are suitable to be used in a computed tomography (CT) device, a flat panel detector (FPD) or the like applied in the medical field and using X-rays.

BACKGROUND ART

For example, in the medical field, a CT device that performs tomography by using X-ray projection data, and an X-ray FPD device that monitors an X-ray projection image as a moving image are utilized, and pixel increase (data volume increase) and acceleration of various kinds of arithmetic processing are in progress in these devices (see Patent Document 1, for example).

Generally, in an X-ray detection unit of a CT device, used is an array of pixels in each of which a scintillator to generate fluorescence (scintillation light) in response to incidence of X-rays is incorporated with a photodiode (PD) that performs photoelectric conversion in response to the light (scintillation light in this case).

In each pixel, the scintillation light generated in response to the X-ray irradiation is converted to electric charge by the PD, and the electric charge is converted to a voltage value via an amplifier, an integrating circuit, and the like, and the voltage value is converted to a digital value by an AD converter of a data acquiring system (DAS) externally attached via a multiplexer, and the digital value is detected as an X-ray irradiation amount.

Note that one pixel in the above-mentioned CT device has a size of a rectangle having one side of about 0.3 to 1 mm, and a single PD is normally formed in each pixel. Since current generated by photoelectric conversion is extremely weak relative to parasitic capacitance of the PD, a current integration process of about 1 millisecond is required to detect the current.

Furthermore, acceleration of examination using the CT device is expected, and a time to photograph a subject while making one revolution around the subject is to be 0.5 seconds or less. To keep an appropriate spatial resolution at such a speed, it is necessary to increase a sampling rate of the X-ray detection unit, and it is necessary to shorten a detection period. For example, in a case where each pixel performs 1000 times of sampling during a revolution period of 0.5 seconds, the detection period is needed to be shortened to 0.5 msec.

CITATION LIST

Patent Document

Patent Document 1: Japanese Patent Application Laid-Open No. 2003-202303

SUMMARY OF THE INVENTION

Problems to be Solved by the Invention

In a case of increasing a sampling rate by shortening a detection period, there is a limit in PD sensitivity, and therefore, it may be possible to conceive a method of increasing an X-ray radiation dose to irradiate a subject, but in this method, an X-ray (X-ray) exposure dose to a test body as the subject is increased.

The present disclosure is made in view of such a situation and is directed to achieving improvement in a sampling rate and spatial resolution without increasing the exposure dose to the subject.

Solutions to Problems

An X-ray detection device according to an aspect of the present disclosure is arranged in a manner facing an X-ray irradiation device while interposing a subject and generates X-ray two-dimensional projection data of the subject, the X-ray detection device including: a scintillator adapted to generate scintillation light in response to incident X-rays; a detection unit including a plurality of pixels each generating a pixel signal in response to the scintillation light incident thereon; and an output unit adapted to generate the X-ray two-dimensional projection data by using the pixel signals of the pixels, in which the pixel of the detection unit includes: a plurality of subpixels adapted to perform photoelectric conversion in response to the scintillation light; an AD conversion unit adapted to apply AD conversion to outputs of the subpixels; and an adder adapted to generate the pixel signal corresponding to the pixel by adding up outputs of the plurality of subpixels after the AD conversion.

The AD conversion unit can apply AD conversion to an output of the subpixel to obtain a value having a gradation of at least 3 bits or more.

The AD conversion unit can be shared by two or more of the subpixels.

The subpixel can include: a photoelectric conversion unit adapted to perform photoelectric conversion in response to the scintillation light, and store electric charge; a holding unit adapted to hold the electric charge transferred from the photoelectric conversion unit; and a first reset unit adapted to reset the photoelectric conversion unit and the holding unit.

The subpixel can further include a second reset unit adapted to reset the photoelectric conversion unit not via the holding unit.

The photoelectric conversion unit of the subpixel can be completely depleted by the first or the second reset unit.

A plurality of different exposure periods can be set for the subpixels by adjusting timing to reset the photoelectric conversion unit.

The output unit can generate the X-ray two-dimensional projection data by combining the pixel signals based on outputs of the subpixels having different exposure periods.

The output unit can perform X-ray counting by discriminating energy while using the pixel signal of the pixel.

The output unit further can perform, per the pixel, integration of outputs in response to a plurality of times of X-ray irradiation.

The output unit can generate the X-ray two-dimensional projection data by adopting one or a combination of both of: a result of X-ray counting by discriminating energy while using the pixel signal of the pixel; and a result of performing, per the pixel, integration of pixel signals corresponding to the plurality of times of X-ray irradiation.

A detection method according to an aspect of the present disclosure is a detection method of an X-ray detection device that is arranged in a manner facing an X-ray irradiation device while interposing a subject and generates X-ray two-dimensional projection data of the subject, and the X-ray detection device includes: a scintillator adapted to generate scintillation light in response to incident X-rays; a detection unit including a plurality of pixels each generating a pixel signal in response to the scintillation light incident thereon; and an output unit adapted to generate the X-ray two-dimensional projection data by using the pixel signals of the pixels, the pixel includes a plurality of subpixels, the detection method being executed by the pixel, including: a photoelectric conversion step of performing, by the plurality of subpixels, photoelectric conversion in response to the scintillation light; an AD conversion step of applying AD conversion to outputs of the subpixels; and an adding-up step of generating the pixel signal corresponding to the pixel by adding up outputs of the plurality of subpixels after the AD conversion.

In one aspect of the present disclosure, photoelectric conversion is performed by a plurality of subpixels constituting a pixel in response to scintillation light, and outputs of the subpixels are subjected to AD conversion, and then a pixel signal corresponding to each pixel is generated by adding up the outputs of the plurality of subpixels after the AD conversion.

Effects of the Invention

According to the first and second aspects of the present disclosure, it is possible to improve a sampling rate and spatial resolution without increasing an exposure dose to a subject.

BRIEF DESCRIPTION OF DRAWINGS

FIG. 9 is a diagram illustrating exemplary outputs of subpixels.

FIG. 10 is a diagram illustrating two-dimensional X-ray projection data.

MODE FOR CARRYING OUT THE INVENTION

In the following, the best mode (hereinafter referred to as an embodiment) to implement the present disclosure will be described in detail with reference to the drawings.

Exemplary Structure of X-Ray CT Device According to First Embodiment

Figure 1:
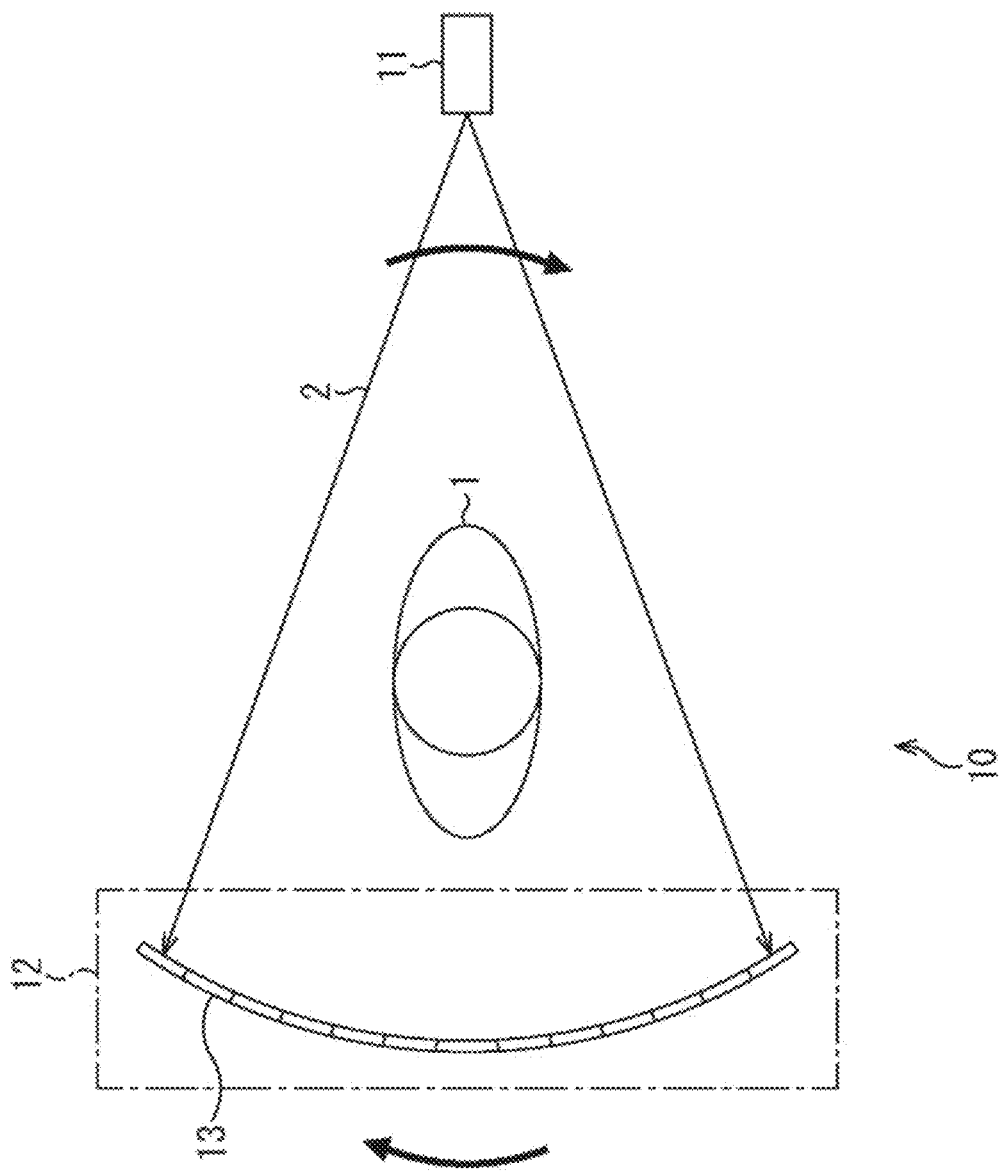
FIG. 1 is a bird's-eye view illustrating an exemplary configuration of an X-ray CT device to which the present disclosure is applied.

FIG. 1 illustrates a bird's-eye view of an X-ray CT device according to a first embodiment to which the present disclosure detection device is applied.

The X-ray CT device 10 is formed of an X-ray irradiation device 11 and a detection device 12 which are arranged in a manner facing each other while interposing a subject 1 in a center therebetween. The X-ray irradiation device 11 and the detection device 12 perform imaging while being driven in a manner revolving around the subject 1.

In other words, the X-ray irradiation device 11 irradiates the subject 1 with photons 2 of X-rays by moving a position in a depth direction of the drawing every revolution around the subject 1, or by moving a position in the depth direction of the drawing while revolving around the subject 1. The detection device 12 acquires X-ray two-dimensional projection data by detecting X-ray photons 2 having passed through the subject 1. Moreover, the detection device acquires three-dimensional tomographic data by back projection processing on two-dimensional projection data.

The detection device 12 includes a detection panel 13 arranged in an arc shape. In the detection panel 13, for example, a plurality of pixels is arranged at 400 μm pitch in 32 rows×64 columns, and a column direction is formed along the arc, and a row direction is formed in the depth direction of the drawing. In this case, the X-ray CT device 10 can perform tomographic imaging for 64 slices of the subject 1.

Figure 2:
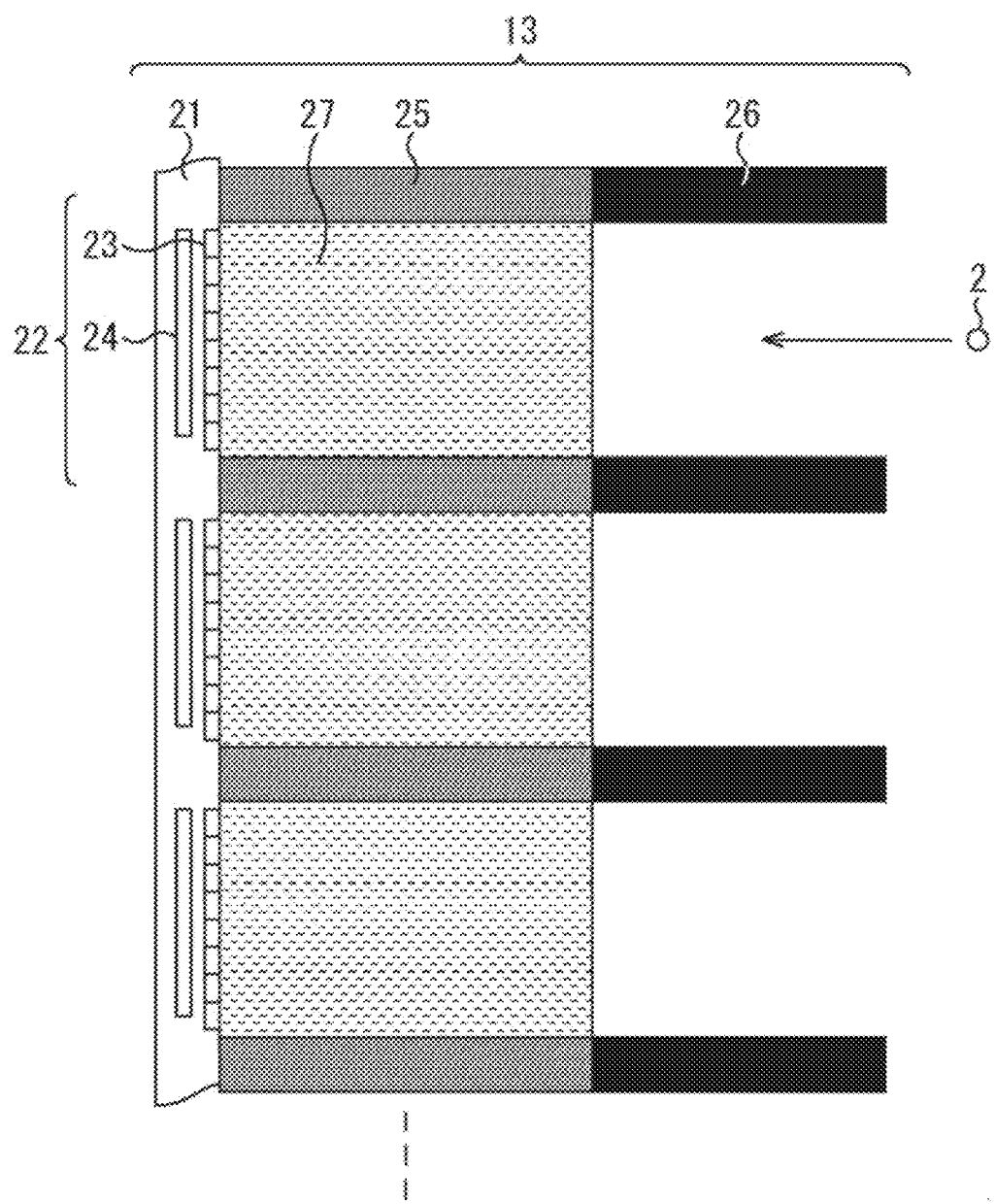
FIG. 2 is a cross-sectional view illustrating an exemplary configuration of a detection panel in FIG. 1.

FIG. 2 is a cross-sectional view illustrating an exemplary configuration of the detection panel 13. The detection panel 13 includes a semiconductor photo-detection unit 21, a partition wall 25, a collimator 26, and a scintillator 27.

The semiconductor photo-detection unit 21 is formed as one chip by stacking: a first silicon layer 23 that is a silicon chip having a plurality of subpixels 31 formed corresponding to one pixel 22 of the detection device 12 (FIG. 3); and a second silicon layer 24 formed with a signal detection unit 41 including an AD conversion circuit to apply AD conversion to output of the subpixel 31 (FIG. 4), and the like. Accordingly, since an output from the external semiconductor photo-detection unit 21 to the outside is digitized, it is possible to prevent influence of external noise unlike a system in the related art in which an AD conversion unit is externally attached.

Here, the subpixel 31 is an extremely sensitive light receiving element and has a circuit configuration and a device structure similar to those of a pixel of a CMOS image sensor used in a digital camera or the like.

Figure 3:
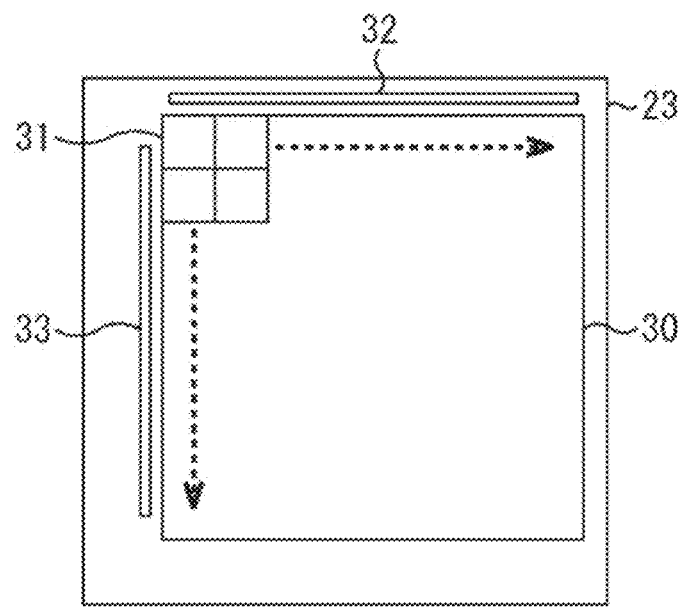
FIG. 3 is a block diagram illustrating an exemplary configuration of a first silicon layer.

FIG. 3 illustrates an exemplary configuration of the first silicon layer 23 corresponding to one pixel 22. In the first silicon layer 23, the plurality of subpixels 31 and connecting portions 32 and 33 to connect the first silicon layer 23 to the second silicon layer 24 are arranged.

Each subpixel 31 has a built-in PD, and an array corresponding to one pixel 22 is constituted by the subpixels 31 arranged in 8 rows×8 columns. Each subpixel 31 has a size of, for example, 40 μm square, and in this case, a size of a light receiving surface 30 as one pixel 22 is 320 μm square. Note that each pixel 22 is arranged at a pitch of 400 μm, and therefore, a physical numerical aperture is $(40×8)^2/400^2=0.64$.

However, in a case where a thickness of the partition wall 27 formed between the respective pixels 22 is 80 μm, a diameter of the scintillator 27 is 320 μm, and therefore, if the scintillator 27 of each pixel 22 is formed in a manner aligned on the light receiving surface 30, most of scintillation light generated by the scintillator 27 of each pixel 22 can be incident on the light receiving surface 30.

The connecting portion 32 connects each subpixel 31 to the signal detection unit 41 formed on the second silicon layer 24 via the connecting portion 42. Note that the connecting portion 32 and the connecting portion 42 are connected via a through silicon via, for example, a metal pad such as Cu.

The connecting portion 33 connects each subpixel 31 to a drive unit 44 formed on the second silicon layer 24 via a connecting portion 43. Note that the connecting portion 33 and the connecting portion 43 are connected via a through silicon via, a metal pad, or the like.

In other space of the first silicon layer 23, a power supply line, a ground line, a signal line, and the like are mainly provided.

Note that the array of subpixels 31 is provided with many kinds of wiring to drive and output therein, and preferred is a back-illuminated type in which each subpixel 31 has a light receiving surface formed on the scintillator 27 side such that the wiring does not interfere with incidence of scintillation light on the subpixel 31 and wiring layers are formed in the first silicon layer 23.

Figure 4:
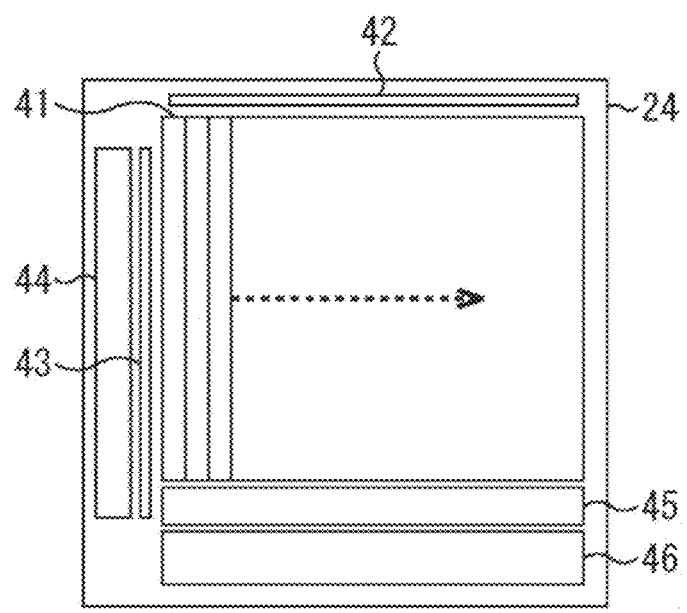
FIG. 4 is a block diagram illustrating an exemplary configuration of a second silicon layer.

FIG. 4 illustrates an exemplary configuration of the second silicon layer 24 corresponding to one pixel 22. In the second silicon layer 24, the signal detection unit 41 including the AD conversion circuit, the drive unit 44 to control driving of subpixels 31, an output processing unit 45 to add up output signals of the respective subpixels 31 subjected to AD conversion and generate an output value of each pixel 22, and a logic control unit 46 to control operation timing of each unit are arranged.

The signal detection unit 41 applies AD conversion to an output of a subpixel 31 to obtain a value having a gradation of at least 3 bits or more. Thirty-two signal detection units 41 are arranged at a pitch of 10 μm and simultaneously detect and sample outputs from thirty-two subpixels. In other words, each signal detection units 41 is shared by two subpixels 31. Note that each signal detection unit 41 may be shared by three or more subpixels 31. Furthermore, one signal detection units 41 may be solely used by one subpixel 31.

Note that in a case where there is a subpixel 31 that malfunctions, the malfunction is detected by the output processing unit 45, and therefore, such a malfunctioning subpixel 31 may be masked and excluded from an added value. Since an output of a pixel 22 is formed of output values of sixty-four subpixels 31, in a case where two of the subpixels are destroyed by X-ray incidence, for example, influence is 5% or less even the subpixels are masked. In this case, correction may be made on outputs corresponding to the number of defective subpixels, if necessary. In other words, assuming that the number of subpixels 31 in a pixel 22 is defined as N and the number of defective subpixels is defined as D, an added-up output value of the (N–D) number of subpixels 31 excluding the defective pixel may be multiplied by a correction value of N/(N–D) so as to obtain an added-up output.

The description is returned to FIG. 2. The partition wall 25 is formed of a material that reflects light between the respective pixels 22, and prevents leakage of scintillation light generated by the scintillator 27 of each pixel 22. The collimator 26 added to each partition wall 25 is made of lead or the like, and blocks incidence of the X-ray photons 2 in an oblique direction. Note that the collimator 26 may be formed depending on necessity, and may also be omitted.

A scintillator 25 formed between the partition walls 25 generates scintillation light in response to incidence of the X-ray photons 2.

The scintillation light generated in each pixel 22 of the detection device 12 is photoelectrically converted by a plurality of subpixels 31 in each pixel 22 and stored as electric charge in the respective subpixels 31. An output signal of each subpixels 31 proportional to the storage amount is subjected to AD conversion at the signal detection unit 41, and an added-up output value of the plurality of subpixels 31 corresponding to one pixel 22 is derived as intensity of the scintillation light incident on the pixel 22.

Figure 5:
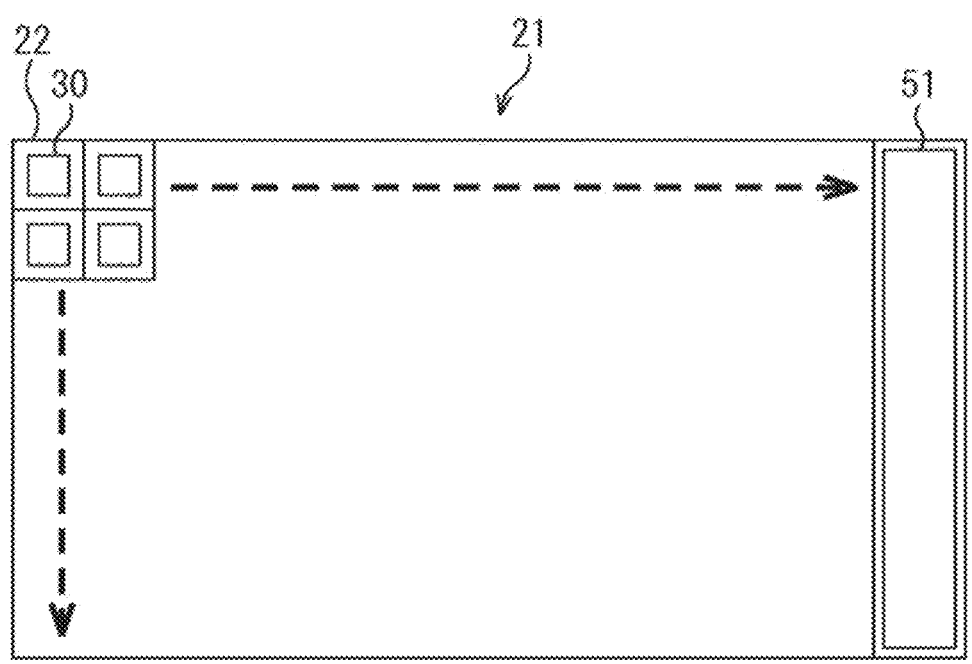
FIG. 5 is a diagram illustrating an exemplary entire configuration of a silicon chip constituting a semiconductor photo-detection unit.

Next, FIG. 5 is a diagram illustrating an exemplary entire configuration of a silicon chip constituting the semiconductor photo-detection unit 21. In the semiconductor photo-detection unit 21, an array is formed by arranging pixels 22 in 32 rows×64 columns at a pitch of 400 μm. An output unit 51 of the array in which the plurality of pixels 22 is arranged, connection pads, and the like are arranged. The output unit 51 generates X-ray two-dimensional projection data on the basis of outputs of the plurality of pixels 22, and outputs the two-dimensional projection data to a subsequent stage.

<Exemplary Structure of Subpixel 31>

Figure 6:
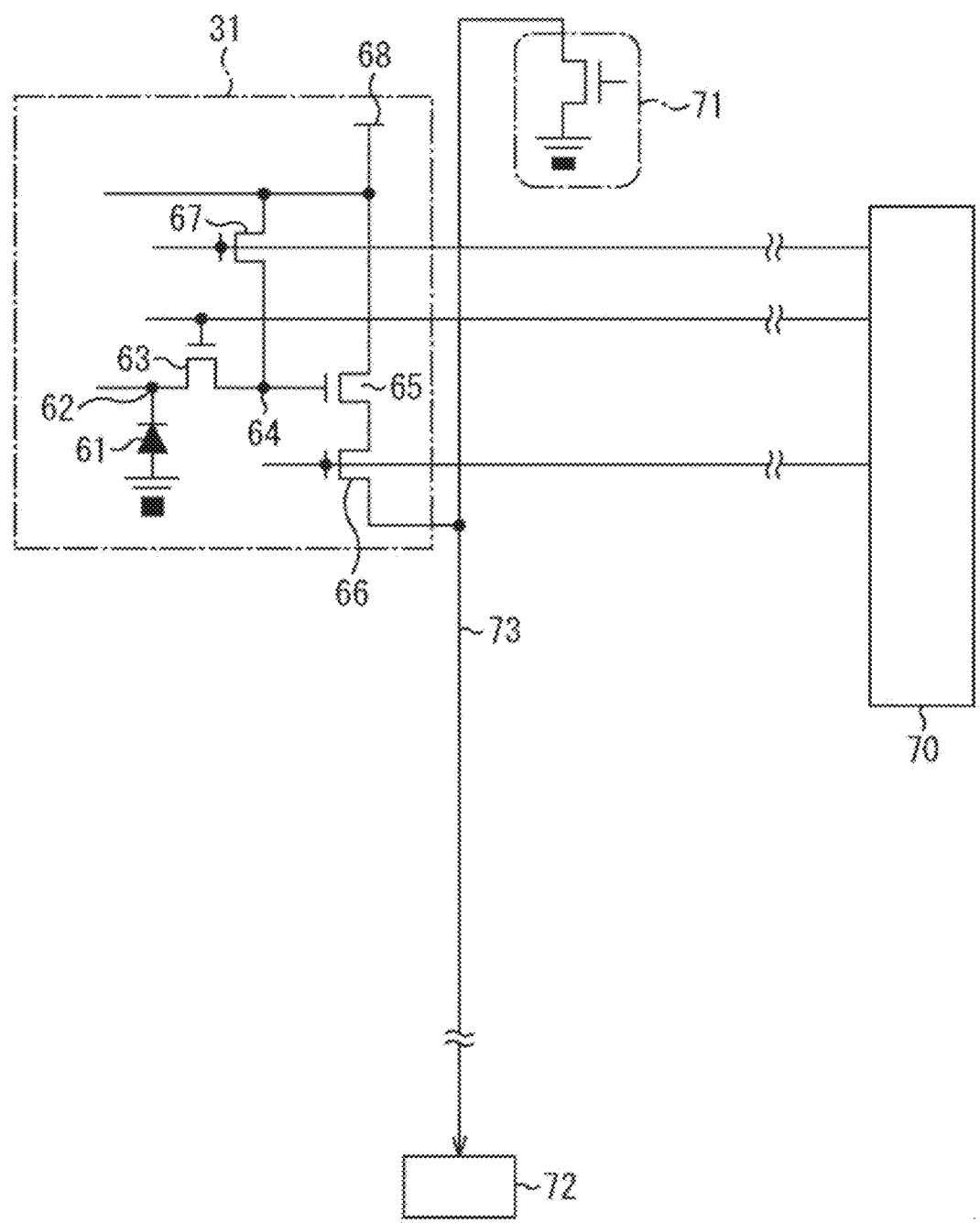
FIG. 6 is an equivalent circuit diagram illustrating an exemplary configuration of a subpixel.

FIG. 6 is an equivalent circuit diagram illustrating an exemplary configuration of a subpixel 31.

The exemplary configuration of the subpixel 31 includes a PD 61, a storage node 62 forming a cathode of the PD 61, a transfer transistor (Tr) 63, a detection node (floating diffusion (FD)) 64, an amplification Tr 65, a selection Tr 66, and a reset Tr 67. For the transfer Tr 63 to the reset Tr 67, for example, n-type metal-oxide semiconductor (MOS) transistors are used.

The PD 61 converts incident photons into electric charge, and stores the same in the storage node 62 functioning as the cathode thereof. More specifically, a pair including an electron and a hole is generated in response to incidence of photons of scintillation light generated by the scintillator 27, and the electron thereof is stored in the storage node 62. Furthermore, the PD 61 is an embedded type in which the storage node 62 is completely depleted at the time of discharging electric charge by resetting. In other words, when the storage node 62 is reset, all of carriers are discharged and a potential of the storage node is fixed only by fixed electric charge by a donor or an acceptor. At this point, even in a case where a node having a deeper potential is connected thereto, the potential of the storage node 62 is not changed.

The transfer Tr 63 transfers the electric charge stored in the storage node 62 to the detection node 64 in accordance with control from a row drive unit 70 included in the drive unit 44. The detection node 64 stores the electric charge transferred via the transfer Tr 63, and generates voltage of an analog value corresponding to the stored electric charge amount. The voltage is applied to a gate of the amplification Tr 65.

The amplification Tr 65 has a gate connected to the detection node 64, a drain connected to a power supply line 68, and a source connected to the selection Tr 66, and drives a vertical signal line 73 having a heavy load via the selection Tr 66 in accordance with voltage applied to the gate. Note that the amplification Tr 65 forms a source follower together with a constant current unit 71 included in the signal detection unit 41, and voltage fluctuation of the detection node 64 is transmitted to the vertical signal line 73 with a gain of less than 1, and an electric signal of this voltage is output to a detection unit 72 included in the signal detection unit 41.

The selection Tr 66 has a gate connected to the row drive unit 70, a drain connected to the amplification Tr 65, and a source connected to the vertical signal line 73, and outputs an electric signal from the amplification Tr 65 to the vertical signal line 73 in accordance with control from the row drive unit 70. Note that, in a case where a subpixel 31 and the detection unit 72 are installed on a one-to-one basis, the selection Tr 66 may be omitted and the source of the amplification Tr 65 may be directly connected to the vertical signal line 73.

The reset Tr 67 has a gate connected to the row drive unit 70, a drain connected to the power supply line 68, and a source connected to the detection node 64, and the electric charge stored in the detection node 64 or the storage node 62 is discharged to the power supply line 68, thereby initializes each thereof.

The row drive unit 70 controls, for example, the reset Tr 67 and the transfer Tr 63 to be turned on at the same time, thereby discharging electrons stored in the storage node 62 to the power supply line 68 and initializing each subpixel 31 to a dark state before electric charge storage, in other words, to a state in which photons of scintillation light have not yet been incident. Furthermore, the row drive unit 70 controls only the reset Tr 67 to be turned on, thereby discharging electric charge stored in the detection node 64 to the power supply line 68 and initializing the electric charge amount.

A subpixel 31 stores the photoelectrically-converted electric charge during a period from when the PD 62 is reset until reading is performed, and then outputs an electric signal of voltage corresponding to the electric charge stored during the reading. When photons of the scintillation light are incident while electric charge is stored by repeating storage and reading during such a unit period, an output result corresponding to a light amount can be obtained during the reading.

Meanwhile, the embedded PD 61 adopted in the subpixel 31 is characterized in that the storage node 62 that is the cathode thereof is not capacitively coupled to the detection node 64 during the reading. As a result, the more reduced parasitic capacitance of the detection node 64 is, the more improved conversion efficiency is, and sensitivity to one-photon incidence can be improved. Additionally, since the conversion efficiency is not deteriorated even in a case where the PD 61 is increased in size, sensitivity of each subpixel 31 for the same luminous flux density can be more improved in a case where the PD 61 is more upsized.

Furthermore, since the subpixel 31 is free from electron multiplication, an output of the subpixel 31 is influenced by reading noise caused by the amplification Tr 65 and the AD conversion unit included in the signal detection unit 41 in the subsequent stage, but in a case where sensitivity of the subpixel 31 is maximized, influence of reading noise can be relatively minimized as described above. In other words, since an SN ratio of an output is maximized by reducing the parasitic capacitance of the detection node 64 as much as possible and upsizing the PD 61 as much as possible within a range where one electron can be moved by drift inside thereof, a subpixel 31 as an ultrahigh sensitivity detector can be implemented.

The structure of the subpixel 31 adopting the PD 61 having such a full-depletion type storage node 62 significantly differs from a PD structure in the related art used in existing X-ray transmission imaging. Since the subpixel 31 responds accurately even to incidence of a small amount of photons and actuates in accordance with a sequence described later, it is possible to quickly output a voltage electric signal to the detection unit 72.

Note that the structure of the subpixel 31 is similar to a pixel structure of a CMOS image sensor used in existing digital cameras or the like, but design philosophy is completely different. The reason for forming an array by arranging a plurality of subpixels 31 inside a pixel 22 is not to obtain spatial resolution therein but to allow the pixel 22 to have a light receiving surface and a physical aperture each having a sufficient size while using the subpixels 31 each having the limited size.

The larger the area of the subpixel 31 is, the more easily the area of the PD 61 is enlarged and the more the numerical aperture is increased, and the number of subpixels 31 sharing the detection unit 72 is reduced and high-speed operation is easily achieved. Furthermore, floor noise per aperture area in the pixel 22 is also reduced. Accordingly, it is preferable that the area of the subpixel 31 be at least 100 $\mu m^2$ or more, more preferably, 400 $\mu m^2$ or more.

An upper limit of the area of the subpixel 31 at the time of upsizing the subpixel 31 is defined by movement of electrons by the drift inside the embedded PD 61, and it is necessary to design a potential inside the PD 61 such that one electron generated at a far end inside the upsized PD 61 is transferred to the detection node 64 with a high speed.

Meanwhile, it has been described that an N type diffusion layer that is a cathode of the PD 61 is formed as the storage node 62 to store electrons, but all polarities may be reversed and a P type diffusion layer that is an anode thereof may also be formed as the storage node 62 to store positive holes.

<First Operation Sequence of Subpixel 31>

Figure 7:
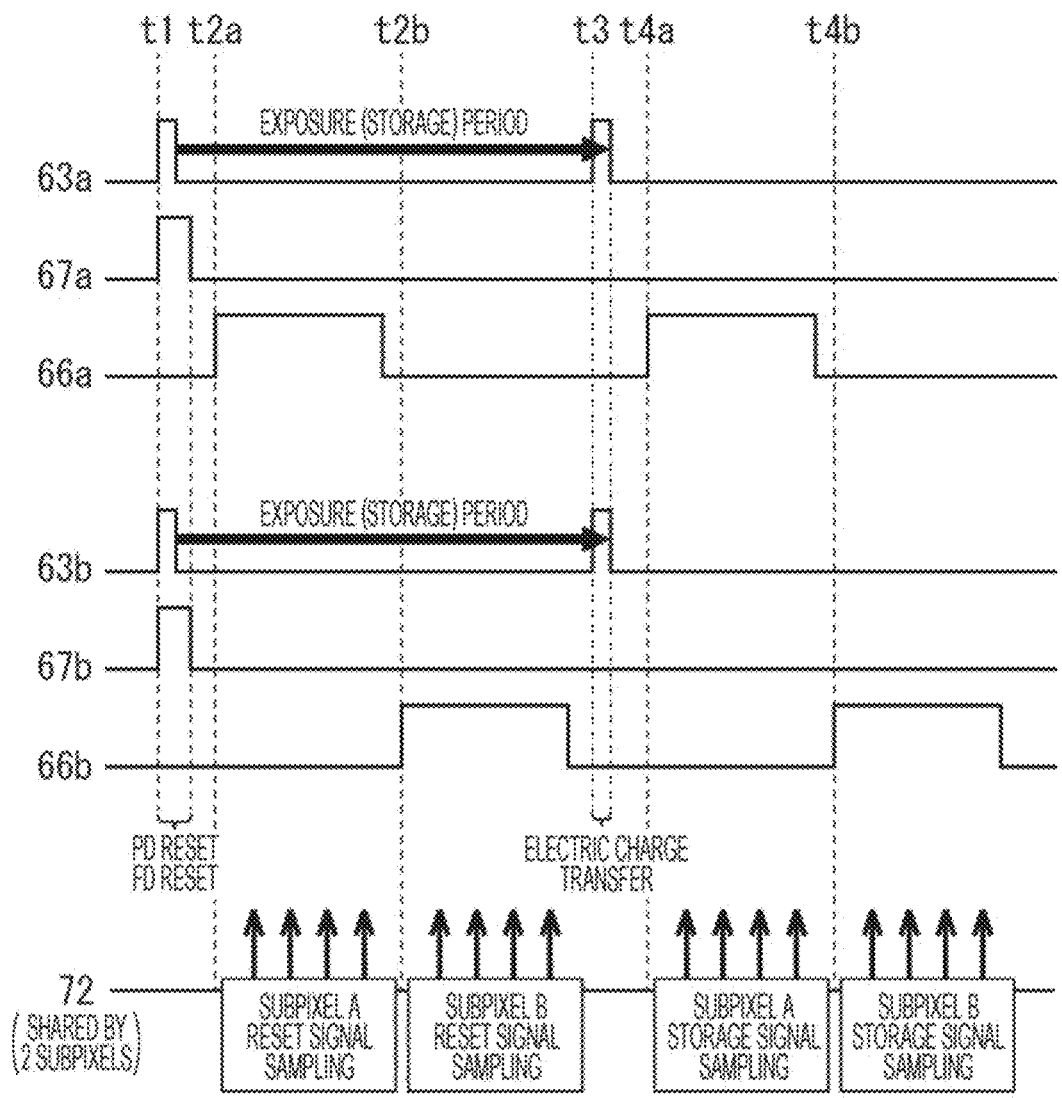
FIG. 7 is a timing chart illustrating a first operation sequence.

Next, FIG. 7 illustrates exemplary operation (first operation sequence) of the subpixel 31.

Note that an upper side of the drawing illustrates an operation sequence of a subpixel 31a out of subpixels 31a and 31b sharing the signal detection unit 41, and a lower side thereof illustrates an operation sequence of the subpixel 31b. For example, 63a on the upper side in the drawing represents ON/OFF states of a transfer Tr 63 in the subpixel 31a. Furthermore, 67b on the lower side of the drawing represents ON/OFF states of a reset Tr 67 in the subpixel 31b.

The detection unit 72 illustrated in FIG. 6 is connected to the two subpixels 31a and 31b via the vertical signal line 73, and alternately performs selection and sampling of an output. As for the sampling, sampling of a reset signal corresponding to the dark state in which photons of scintillation light have not yet been incident, and sampling of a stored signal after an exposure period are performed, and correlated double sampling (CDS) for cancelling various kinds of noise is executed by obtaining a difference therebetween.

First, the row drive unit 70 simultaneously controls the transfer Trs 63a and 63b and the reset Trs 67a and 67b to be turned ON at timing t1 immediately before a storage period. With this control, electric charge stored in the storage nodes 62a and 62b of the PDs 61a and 61b are all discharged to the power supply line 68 via the detection nodes 64a and 64b. In the following, this control will be referred to as "PD reset".

After that, the row drive unit 70 controls the transfer Trs 63a and 63b to be turned OFF. With this control, the storage nodes 62a and 62b are each brought into a floating state and new electric charge storage is started. Furthermore, after PD reset, the row drive unit 70 controls the reset Trs 67a and 76b to be turned OFF. With this control, potentials of the detection nodes 64a and 64b are slightly lowered from a reference potential due to coupling to the gates of the reset Trs 67a and 67b, and the detection nodes are each brought into the floating state. Moreover, at this point, significant kTC noise is generated in the detection nodes 64a and 64b. Since floating diffusions (FD) are generally used for the detection nodes 64a and 64b, this control will be referred to as "FD reset". In other words, in the first operation sequence, PD reset and FD reset are performed consecutively.

Next, reset signal sampling is sequentially performed for the subpixels 31a and 31b. The reset signal sampling is deemed as first reading in the correlated double sampling.

In other words, the row drive unit 70 controls the selection Tr 66a to be turned ON only for a predetermined period from timing t2a. With this control, the subpixel 31a and the vertical signal line 73 are connected, voltage of the detection node 64a is amplified by the amplification Tr 65a and output to the vertical signal line 73. The detection unit 72 performs sampling once or more (for example, four times). In such sampling, a potential signal of the vertical signal line 73 is converted into a digital signal Ds1a by the detection unit 72 as a reset signal of the subpixel 31a, and is saved in a register inside the detection unit 72.

Next, the row drive unit 70 controls the selection Tr 66b to be turned ON only for a predetermined period from timing t2b. With this control, the subpixel 31b and the vertical signal line 73 are connected by the selection Tr 66b, voltage of the detection node 64b is amplified by the amplification Tr 65b and output to the vertical signal line 73. The detection unit 72 performs sampling once or more (for example, four times). In such sampling, a potential signal of the vertical signal line 73 is converted into a digital signal Ds1B by the detection unit 72 as a reset signal of the subpixel 31b, and is saved in the register inside the detection unit 72.

Then, at timing t3 immediately before finishing the storage period, the row drive unit 70 controls the transfer Trs 63a and 63b to be turned ON. With this control, the electric charge stored in the storage nodes 62a and 62b is transferred to the detection nodes 64a and 64b respectively. At this point, in a case where potentials of the detection nodes 64a and 64b are sufficiently deep, all of the electrons stored in the storage nodes 62a and 62b are transferred to the detection nodes 64a and 64b respectively, and the storage nodes 62a and 62b become a fully depleted state. After a pulse period elapses from timing t33, the row drive unit 70 controls the transfer Trs 63a and 63b to be turned OFF. With this control, the potentials of the detection nodes 64a and 64b are lowered by an amount of the stored electric charge (in other words, the potentials become shallower) compared to those before driving the transfer Trs 63a and 63b.

Next, stored signal sampling is sequentially performed for the subpixels 31a and 31b. The stored signal sampling is deemed as second reading in correlated double sampling.

In other words, the row drive unit 70 controls the selection Tr 66a to be turned ON only for a predetermined period from timing t4a. With this control, the subpixel 31a and the vertical signal line 73 are connected, and the above-described voltage corresponding to the decreased amount is amplified by the amplification Tr 65a and output to the vertical signal line 73.

The detection unit 72 performs sampling once or more (for example, four times). In such sampling, a signal of the potential of the vertical signal line 73 is converted into a digital signal Ds2a by the detection unit 72 as a storage signal of the subpixel 31a. Moreover, the detection unit 72 determines an incident photon amount on the basis of a comparison result obtained by comparing the sampled storage signal (namely, digital signal Ds2a) with the reset signal saved in the register (namely, digital signal Ds1a).

Specifically, all of the plurality of digital signals Ds1a obtained from a plurality of times of sampling is added up or an average value thereof is calculated. Similarly, all of the digital signals Ds2a are also added up or an average value thereof is calculated. The detection unit 72 calculates, as a net storage signal, a difference between the added-up value (or average value) of the digital signals Ds1a and the added-up value (or average value) of the digital signals Ds2a. This calculation result becomes output data corresponding to one-time exposure period in the subpixel 31a. Note that kTC noise generated at the time of FD reset is canceled by setting the difference between a digital signal Ds1a and a digital signal Ds2a as a net storage signal.

Similarly, the row drive unit 70 controls the selection Tr 66b to be turned ON only for a predetermined period from timing t4b. With this control, the subpixel 31b and the vertical signal line 73 are connected, and the voltage corresponding to the decreased amount is amplified by the amplification Tr 65b and output to the vertical signal line 73.

The detection unit 72 performs sampling once or more (for example, four times). In such sampling, a signal of the potential of the vertical signal line 73 is converted into a digital signal Ds2b by the detection unit 72 as a storage signal of the subpixel 31b. Moreover, the detection unit 72 determines an incident photon amount on the basis of a comparison result obtained by comparing the sampled storage signal (namely, digital signal Ds2b) with the reset signal saved in the register (namely, digital signal Ds1b).

Specifically, all of the plurality of digital signals Ds1b obtained from a plurality of times of sampling is added up or an average value thereof is calculated. Similarly, all of the digital signals Ds2b are also added up or an average value thereof is calculated. The detection unit 72 calculates, as a net storage signal, a difference between the added-up value (or average value) of the digital signals Ds1b and the added-up value (or average value) of the digital signals Ds2b. This calculation result becomes output data corresponding to one-time exposure period in the subpixel 31b. Note that kTC noise generated at the time of FD reset is canceled by setting a difference between a digital signal Ds1b and a digital signal Ds2b as a net storage signal.

Meanwhile, the exposure storage period of each subpixel 31 is a period from the above-described PD reset operation to the stored electric charge reading operation in which the electric charge stored in the storage node 62 is transferred to the detection node 64, and more accurately, is a period from when the transfer Tr 63 is turned off after resetting until the transfer Tr 63 is turned off at reading. When photons are incident on the PD 61 during this storage period and electric charge is generated, this causes a difference between the reset signal and the stored signal, and the difference is derived by the detection unit 72 in accordance with the above-described sequence.

In other words, the detection unit 72 has the correlated double sampling function, and low frequency noise of a pixel including kTC noise can be canceled by the correlated double sampling function. Furthermore, noise mixed in the AD conversion process can also be canceled by performing correlated double sampling between digital values in AD conversion errors.

However, in the case of the above-described first operation sequence, high-speed sampling cannot be performed because there is a dead period during which storage is not performed for a period from finish of one-time exposure period to start of a next exposure period, particularly, during the sampling period of a stored signal.

Therefore, the operation sequence (second operation sequence) eliminating such a dead period during which storage is not performed will be described next.

<Second Operation Sequence of Subpixel 31>

Figure 8:
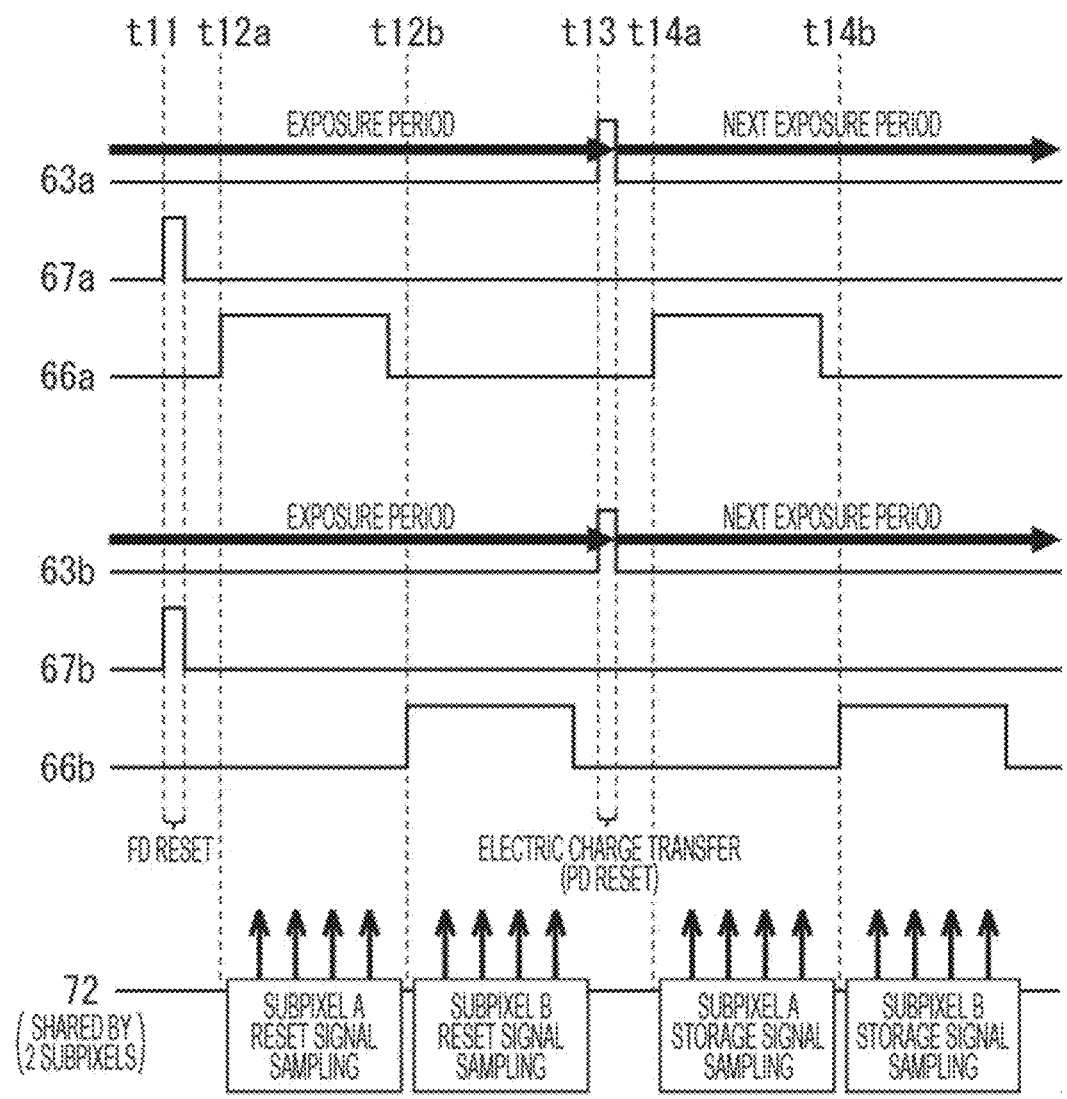
FIG. 8 is a timing chart illustrating a second operation sequence.

Next, FIG. 8 illustrates another exemplary operation (second operation sequence) of the subpixel 31.

Note that an upper side of the drawing illustrates an operation sequence of a subpixel 31a out of subpixels 31a and 31b sharing the signal detection unit 41, and a lower side thereof illustrates an operation sequence of the subpixel 31b. For example, 63a on the upper side in the drawing represents ON/OFF states of a transfer Tr 63 in the subpixel 31a. Furthermore, 67b on the lower side of the drawing represents ON/OFF states of a reset Tr 67 in the subpixel 31b.

In the second operation sequence illustrated in FIG. 8, PD reset at timing t1 of the first operation sequence is omitted and PD reset is performed when electric charge is transferred to the detection node 64 from the storage node 62.

In other words, only the FD reset is performed at timing t11 of the second operation sequence, and reset level sampling is performed at timing t12a and timing t12b. In other words, no pulse is applied to the transfer Trs 63a and 63b at the timing t11, and stored electric charge of the storage node 62 is held as it is. After that, pulses are applied to the transfer Trs 63a and 63b at timing t13 to transfer electric charge from the storage node 62 to the storage detection node 64, but this electric charge transfer also serves as PD reset. At this point, a next storage period of the PD 31 starts immediately after this electric charge transfer serving as the PD reset. Consequently, a dead period during which no incident photon on the pixel is detected can be substantially eliminated, and high-speed sampling can be achieved.

Note that, in both of the first and second operation sequences, a shortest period per unit storage is defined by a total required time for reset level sampling and storage level sampling. However, the storage time in the first operation sequence is about half of the storage time in the second operation sequence.

In the first operation sequence, an effective exposure time, that is, the storage time is reduced by the electric charge being discharged on the halfway at timing t1. For example, assuming that the above-mentioned total required time for sampling per subpixel 31 is 15 μ seconds, in a case where two subpixels 31 share the detection unit 72, the detection unit 72 requires 30μ seconds in order to obtain an output corresponding to one-time exposure period. Such sampling is simultaneously executed in parallel by a plurality of detection units 72, and outputs thereof are instantaneously added up per pixel 22 and output as sample data of each pixel 22. In this case, a sampling rate of the pixel 22 can achieve a high speed of about 33,000 Hz.

Meanwhile, since the signal detection unit 41 including the AD conversion circuit and the array of the subpixels 31 are formed as one chip as illustrated in FIG. 2, a correspondence relation between each subpixel 31 and the signal detection unit 41 has no change even in a case where the number of slices and the number of channels are increased, in other words, even in a case where the number of pixels 22 is increased. Those are simultaneously operated in parallel, and digital sample data is output per pixel 22. Therefore, even in a case where the number of pixels 22 is increased in order to increase the number of channels and the number of slices, the sampling rate or the number of views of the detection device 12 can be easily maintained.

<Exemplary Output of Subpixel 31>

Next, FIG. 9 illustrates exemplary outputs of some of subpixels 31 arranged in 8 rows×8 columns and constituting one pixel 22.

Here, for example, one photon signal (equivalent to an electronic signal as a signal after photoelectric conversion) corresponds to 10 LSB, and the subpixel 31 outputs combination of a photon signal (one electron per subpixel 31 on average) and reading noise (0.5 electron rms per subpixel).

Note that a minus output may also be generated because noise is combined. In FIG. 9, minus values are described as they are, but all of outputs may be made to plus outputs by applying offset to all thereof or by rounding out a minus value to 0.

In other words, each pixel 22 of the semiconductor photo-detection unit 21 is formed as an aggregate of highly sensitive light detection cells (subpixels 31) each having a gradation output. Generally, the subpixel 31 does not perform electron multiplication by an intense electric field like an avalanche photodiode (APD), a photo-multiplier tube, or the like, and an output signal is minute. Therefore, since significant reading noise is included, the number of incident photons in each subpixel 31 is ambiguous. However, since outputs of the subpixels 31 constituting the pixels 22 are added up, a weak pulse light amount is derived with high accuracy.

In the following, a description will be provided with specific numerical values. The scintillator 27 that generates photons incident on a subpixel 31 generates scintillation light proportional to intensity of incident X-rays. For example, assumed is a case where one X-ray photon 2 with an output of 120 keV is incident on the scintillator 27, and 1000 photons out of the scintillation light generated in response thereto are incident on one pixel 22.

Furthermore, assuming that the reading noise per subpixel 31 is 0.5 electron rms, floor noise of the light receiving surface 30 of one pixel 22 can be estimated as $\sqrt{(0.5^2 \times 8 \times 8)}=4$ electrons rms. Assuming that quantum efficiency of the subpixel 31 is 90%, signal electric charge of 900 electrons (=1000×90%) is generated in response to incidence of 1000 photons. At this point, light shot noise=$\sqrt{(signal\ electric\ charge\ number)}$ is 30 electron rms.

Noise combining the floor noise and the shot noise is $\sqrt{(4^2+30^2)} \approx 30$ electron rms, and a high energy resolution of 7.8%(=2.35×30/900) [FWHM] can be obtained as a half value width. In other words, X-ray counting using energy discrimination can be performed.

Note that the above-described floor noise can be ignored in a multiplication type photo-detector like a photo-multiplier tube, but the floor noise cannot be ignored in a PD 61 adopted in a subpixel 31 of the semiconductor photo-detection unit 21 according to the present embodiment. However, since the PD 61 has a high quantum efficiency in a visible light region, many more photoelectric conversion signals can be acquired according to such efficiency, and influence of light shot noise can be reduced. In a comprehensive viewpoint, the semiconductor photo-detection unit 21 according to the present embodiment can achieve energy resolution equal to or higher than that of a photo-multiplier tube or the like in a region having relatively high radiation dose, such as X-ray transmission imaging.

Note that each subpixel 31 of the semiconductor photo-detection unit 21 according to the present embodiment can store several hundreds of electrons or more, and has a wide dynamic range. For example, in a case where an output of each subpixel 31 is applied with AD conversion at a resolution of 12 bits, the sum of outputs of subpixels 31 arranged in 8 rows×8 columns and constituting one pixel 22 is a resolution of about 12+log 2(8×8)≈18 bits per sample. Note that setting for the above-described LSB value can be easily changed by, for example, using gain application or the like in a preceding stage of a subpixel signal input unit in the AD conversion circuit, and adjustment in accordance with an incident light amount can be performed.

As described above, the semiconductor photo-detection unit 21 in the present embodiment can detect X-rays with super high sensitivity and high speed. Therefore, the X-ray CT device 10 using the semiconductor photo-detection unit 21 can reduce an X-ray radiation dose even in the case of performing photographing similar to the related art, and data with high resolution and high accuracy can be obtained by increasing the number of samples. Moreover, since the semiconductor photo-detection unit 21 is combined with an X-ray irradiation device capable of performing ultrahigh-speed scanning like an electron beam CT that does not require revolving drive around a subject 1, data having accuracy same as the related art can be obtained at extremely high speed with low radiation exposure.

Furthermore, the semiconductor photo-detection unit 21 according to the present embodiment has the sensitivity capable of discriminating energy of one X-ray photon 2, and X-ray projection data can be acquired by X-ray counting using energy discrimination.

By the way, photons of scintillation light detected by each subpixel 31 in response to incidence of one X-ray photon is about 14 (≈900/64) on average. As fluctuation of incident photons, √14 rms is estimated, and signal detection of twenty-nine electrons is required considering ±4 σ.

Furthermore, assuming that quantization noise is suppressed to 1 electron rms or less, 3.5 electrons or less is required as 1 LSB (3.5/√12≈1). Therefore, a resolution of 3 bits or more (≈ $\log_2(29/3.5)$) is also required in AD conversion according thereto.

Furthermore, considering X-ray detection using an integration mode, each subpixel 31 needs to detect energy intensity in a state where a plurality of X-rays is in a pile-up state, and a detection range of one hundred electrons or more is preferred. Therefore, AD conversion is also preferably executed at a resolution of 5 bits or more (≈ $\log_2(100/3.5)$) according thereto.

Additionally, it is preferable that the number of subpixels 31 constituting one pixel 22 be four (=2×2) or more so as to enable defect correction. Furthermore, at most 10000 (=100×100) subpixels, if possible, 1600 (=40×40) subpixels or less are preferable so as to sufficiently reduce floor noise integrated along with size increase of the pixels 22.

For example, in a case where one pixel 22 is formed by arranging 10000 (=100×100) subpixels 31 each having an area of 100 pmt or more, the area of one pixel 22 becomes 1 mm$^2$ or more, and therefore, it is preferable that the number of subpixels 31 constituting one pixel 22 be 10000 (=100×100) or less from the viewpoint of spatial resolution in the semiconductor photo-detection unit 21.

Next, FIG. 9 illustrates two-dimensional X-ray projection data sampled by each pixel 22.

In other words, intensity data of incident X-rays sampled by each pixel 22 is developed into two-dimensional X-ray projection data as illustrated in the drawing in which an X axis is set as a body axis direction of a subject 1 and a Y axis is set as a revolving direction of the X-ray irradiation device 11 and the detection device 12.

In the case of processing this two-dimensional X-ray projection data with a resolution corresponding to a pixel pitch, the number of sampling data NS reflected in one pixel section on the X-ray projection data per revolution of the X-ray irradiation device 11 and the detection device 12 can be estimated as expressed in a following Expression.

$$NS=RS \cdot \tau \cdot \gamma/360$$

Here, τ represents a time [sec] required per revolution, γ represents a fan angle [degree] of the semiconductor photo-detection unit 21, and RS represents a sampling rate [Hz] of the semiconductor photo-detection unit 21.

For example, in a case of setting the required time per revolution as τ=0.5 seconds, the fan angle as γ=45 degrees, and the sampling rate as RS=33000 Hz, the number of sampling data becomes NS≈2062.

Assuming that a bit resolution of one-time sampling is set as 18 bits in a case of evaluating X-ray intensity by integration processing, a resolution corresponding to 29 bits in total (≈18+$\log_2$2062) is obtained.

On the other hand, in a case of processing this resolution as a result of X-ray counting, one-time sampling is evaluated as a binary value indicating presence or absence of X-ray incidence, and therefore, a maximum value of counting is equal to the number of times of sampling, and a resolution of only 11 bits (≈ $\log_2$2062) is obtained. Therefore, dynamic range of data acquisition is insufficient in this case.

Moreover, in a case of processing the resolution as a result of X-ray counting, there may be a possibility to cause so-called pile-up in which a plurality of X-ray photons 2 is incident during the same storage period of the same pixel 22 when an incident radiation dose is high. In other words, in a case where pile-up is caused, only the fact of incidence is counted even though the plurality of X-ray photons 2 is incident, and energy discrimination becomes also impossible.

Therefore, in the case of processing the X-ray projection data as a result of X-ray counting, two kinds of methods to improve a dynamic range will be described.

In a first method, it is sufficient that pixels each having a high X-ray reception probability and pixels each having a low X-ray reception probability are provided, and X-ray projection data is formed by combining outputs of both kinds of pixels. With the pixels each having the high X-ray reception probability and the pixels each having the low reception probability, an X-ray reception probability of the same pixel 22 may be changed in a time sharing manner, or pixels each having different X-ray reception probabilities may be arranged in a planar shape.

The semiconductor photo-detection unit 21 according to the present embodiment can dynamically and flexibly set the X-ray reception probabilities.

For example, in the first operation sequence illustrated in FIG. 7, a total exposure period (storage period) is about half compared with that of the second operation sequence illustrated in FIG. 8, and photons of scintillation light based on X-ray incidence during a period other than the exposure period in the first operation sequence are discarded. Therefore, in a case of executing the first operation sequence, the X-ray reception probability becomes about half compared with a case of executing the second operation sequence.

Furthermore, since one reset Tr is added to the exemplary configuration of the subpixel 31 illustrated in FIG. 6, an exposure period can be set more flexibly.

<Modified Example of Subpixel 31>

Figure 11:
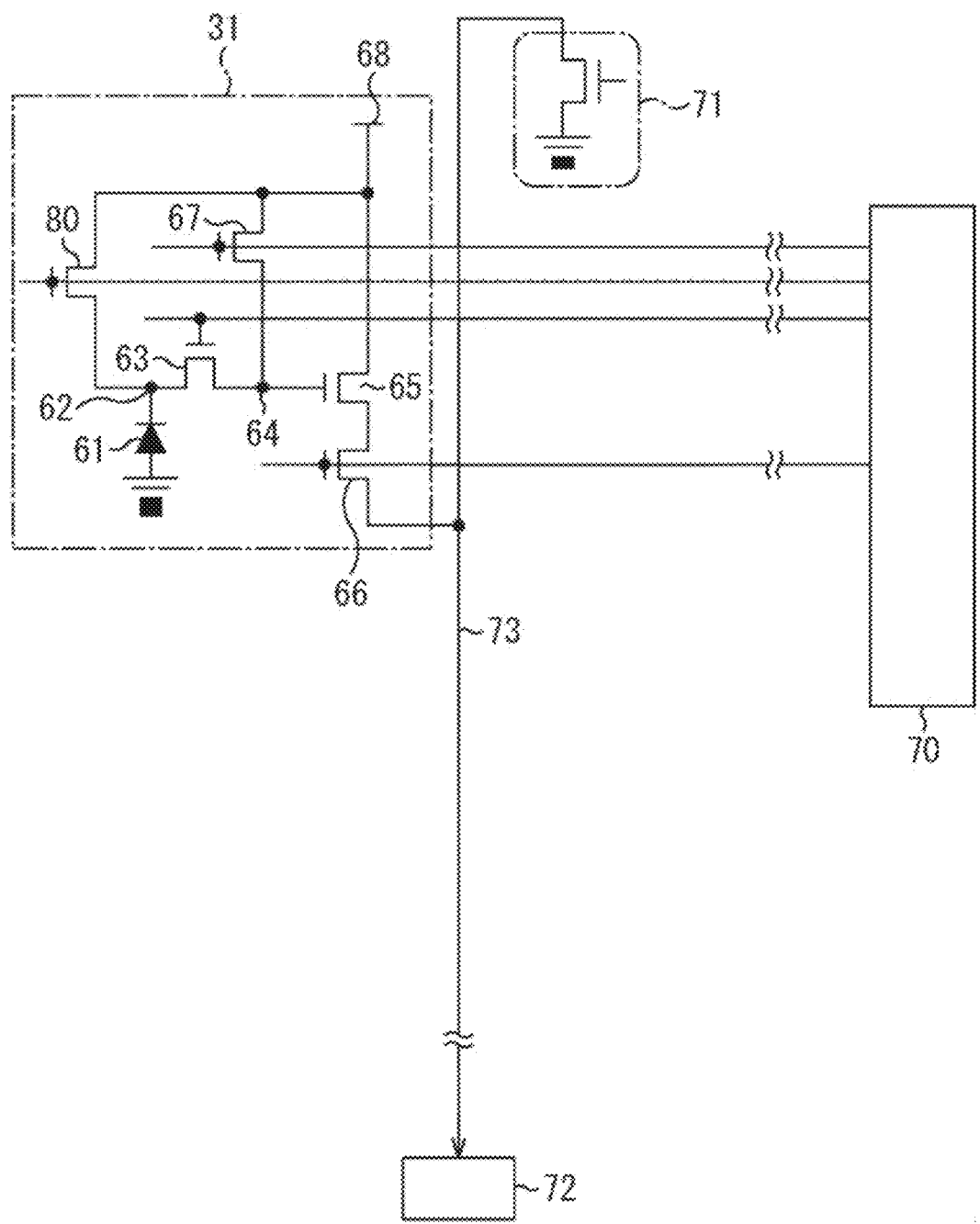
FIG. 11 is an equivalent circuit diagram illustrating a modified example of a subpixel.

FIG. 11 illustrates an equivalent circuit corresponding to a modification example in which a reset Tr 80 is added to the exemplary configuration of the subpixel 31 illustrated in FIG. 6.

The reset Tr 80 has a gate connected to the row drive unit 70, a drain connected to the power supply line 68, and a source connected to the storage node 62 of the PD 61. In other words, when the row drive unit 70 controls the reset Tr 80 to be turned ON, the storage node 62 of the PD 61 is reset at arbitrary timing even though the transfer Tr 63 is in the OFF state, and the storage node can be initialized to a dark state before storage, that is, a state where light has not yet been incident.

<Third Operation Sequence According to Modified Example of Subpixel 31>

Figure 12:
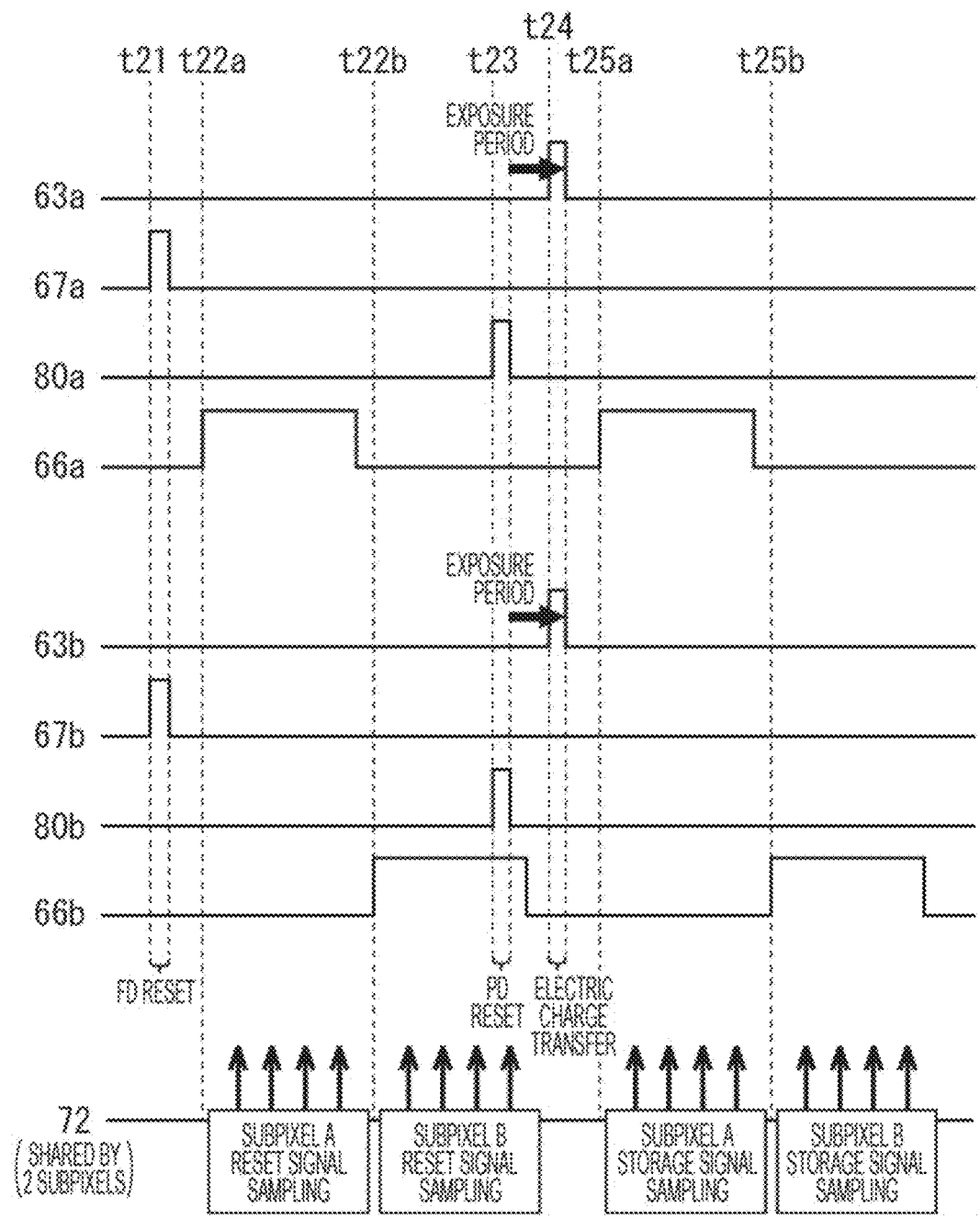
FIG. 12 is a timing chart illustrating a third operation sequence.

Next, FIG. 12 illustrates an exemplary operation (third operation sequence) according to the modified example of the subpixel 31.

In the third operation sequence, a process of directly executing PD reset for the storage node 62 of the PD 61 not via the detection node 64 is added to the first operation sequence illustrated in FIG. 7.

Specifically, for example, PD reset is directly executed at timing t23 by turning on the reset Trs 80a and 80b. Note that PD reset using the reset Tr 80 can be executed at arbitrary timing independently from sampling of a reset signal or a storage signal. The exposure period at this point is a period from when control pulses to the reset Trs 80a and 80b are turned off until control pulses to the transfer Trs 63a and 63b are turned off.

According to the third operation sequence, the exposure period can be set to 100n seconds or less, and therefore, the exposure period can be flexibly adjusted in a wider range.

Figure 13:
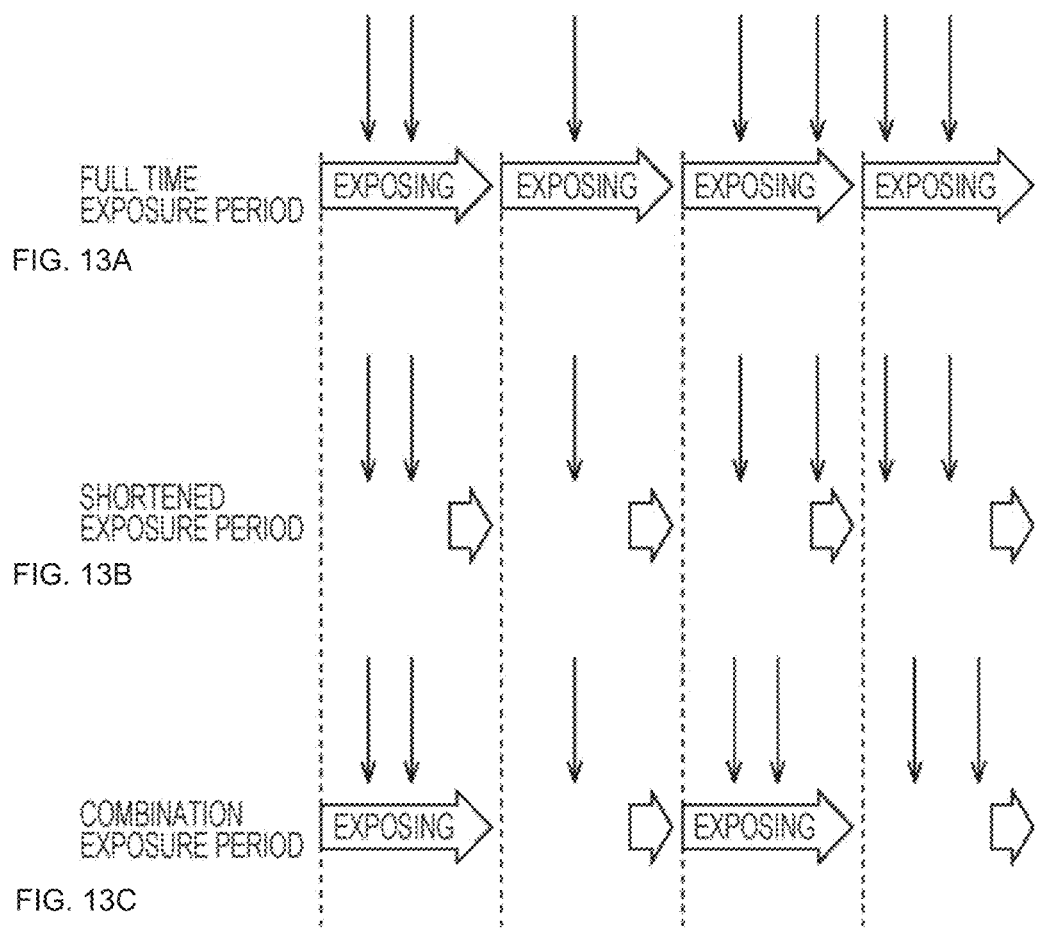
FIGS. 13A, 13B, and 13C illustrate conceptual diagrams illustrating a countermeasure against pile-up.

Next, FIGS. 13A, 13B, and 13C illustrate a concept of a countermeasure against pile-up by shortening an exposure period.

A full time exposure period illustrated in FIG. 13A of the drawing corresponds to the second operation sequence illustrated in FIG. 8. A shortened exposure period illustrated in FIG. 13B of the drawing corresponds to the first operation sequence illustrated in FIG. 7 or the third operation sequence illustrated in FIG. 12. A combination exposure period illustrated in FIG. 13C of the drawing illustrates a case where the full time exposure period and the shortened exposure period are combined in a time sharing manner. Note that the full time exposure period and the shortened exposure period may be spatially mixed. For example, as for a pair of adjacent pixels, the full time exposure period may be set for one pixel and the shortened exposure period may be set for the other pixel.

<Combination of Output of Pixel During Full Time Exposure Period with Output of Pixel During Shortened Exposure Period>

Figure 14:
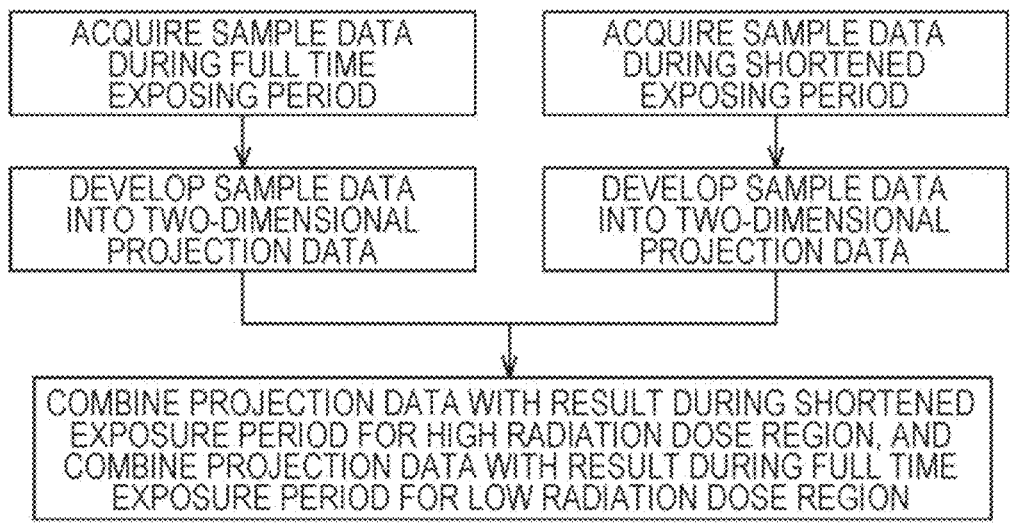
FIG. 14 is a diagram illustrating a sequence corresponding to a first method of improving a dynamic range.

Next, FIG. 14 illustrates a sequence in the case of combining an output of a pixel during the full time exposure period (pixel having high X-ray reception probability) with an output of a pixel during the shortened exposure period (pixel having low X-ray reception probability). Note that the full time exposure period is at least required to have a long exposure period relative to the shortened exposure period, and does not mean to have a longest exposure period that can be set. On the other hand, the shortened exposure period is at least required to have a short exposure period relative to the full time exposure period.

In a scan type device such as an X-ray CT device 10, output data of pixels during the shortened exposure period and output data of pixels during the full time exposure period are mapped in a mixed manner at the same position in the two-dimensionally developed X-ray projection data as illustrated in FIG. 10.

Therefore, the output data of the pixels during the full time exposure period with higher sensitivity is adopted for a low radiation dose region irradiated with low X-ray radiation dose. In contrast, the output data of the pixels during the shortened exposure period, that is hardly saturated, is adopted for a high radiation dose region irradiated with high X-ray radiation.

For example, in the case of X-ray counting, an X-ray radiation dose and probability of pile-up correspond to a counting probability on the basis of Poisson distribution. In a case where the probability of counting X-rays is high in a plurality of times of sampling, a probability of having a high radiation dose and causing pile-up can also be deemed high. Accordingly, output data of the pixels during the full time exposure period is evaluated at first for each region of the X-ray projection data, and in a case where the counting probability is a predetermined threshold value or less, the output data of the pixels during the full time exposure period is directly adopted in this region. In contrast, in a case where the counting probability exceeds the predetermined threshold value, it is sufficient that the output data of the pixels during the shortened exposure period is adopted in the region.

Meanwhile, at the time of combining X-ray projection data, it is preferable to combine the X-ray projection data after multiplying the same by a correction coefficient corresponding to an exposing period. Furthermore, setting for an exposing period is not limited to the two types of the full time exposure period and the shortened exposure period, and outputs of pixels corresponding to three or more kinds of different exposing periods may also be combined.

Next, in a case of processing X-ray projection data as a result of X-ray counting, a second method to improve a dynamic range will be described.

In the second method, diagnosis is executed by using both of X-ray counting data and integral data, and a region where accuracy is lost due to pile-up caused in the X-ray counting data is complemented by using the integral data.

Figure 15:
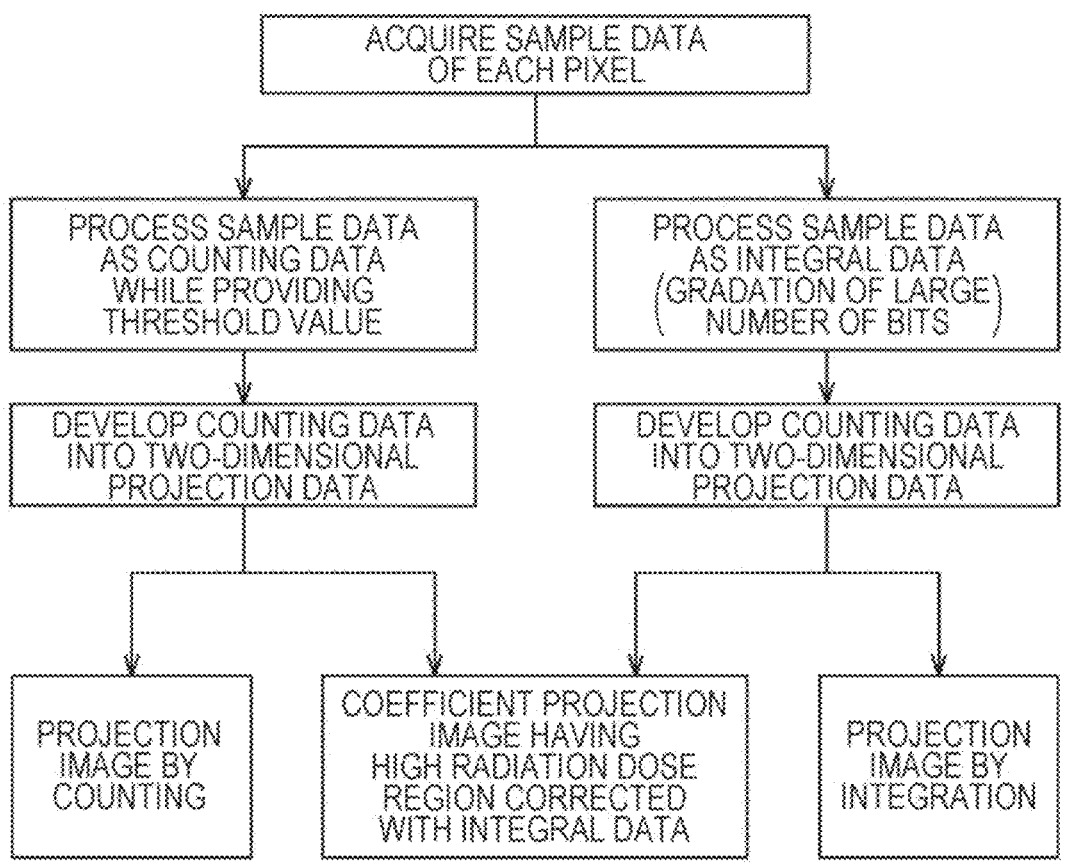
FIG. 15 is a diagram illustrating a sequence corresponding to a second method of improving a dynamic range.

Next, FIG. 15 illustrates an exemplary sequence corresponding to the second method. First, counting processing and integration processing are individually applied to a sample data group acquired from each pixel, thereby acquiring counting data and integral data. Here, the sample data acquired from each pixel is digital gradation data obtained by summing gradation output values from subpixels 31.

In line counting processing on one side, an upper threshold value and a lower threshold value are provided to determine whether or not sample data is within a range between the upper and lower threshold values, and in a case where sample data is determined to be within the range between the upper and lower threshold values, the sample data is counted as 1, and in a case where the sample data is not within the range between the upper and lower threshold values, the sample data is not counted (count as 0). Thus, a large number of pieces of sampled binary data are developed into two-dimensional X-ray projection data.

In the integration processing on the other hand, sample outputs of pixels having gradations are directly mapped on the two-dimensional X-ray projection data. Alternatively, a high radiation dose region on the X-ray projection data mapped with X-ray counting values is corrected and complemented by using mapping data by the integration processing.

For example, in a region where pile-up is caused at many parts, counting is performed by using only the lower limit threshold value, and a counting value is corrected on the basis of a counting rate while using the Poisson distribution. Then, average energy is calculated from the integral data and the corrected counting value, and the counting value is corrected again from comparison between an energy range to be originally counted and the calculated average energy. A three-dimensional tomographic image can be obtained by applying such back projection processing to the X-ray two-dimensional projection data.

Exemplary Structure of X-Ray FPD Device According to Second Embodiment

Figure 16:
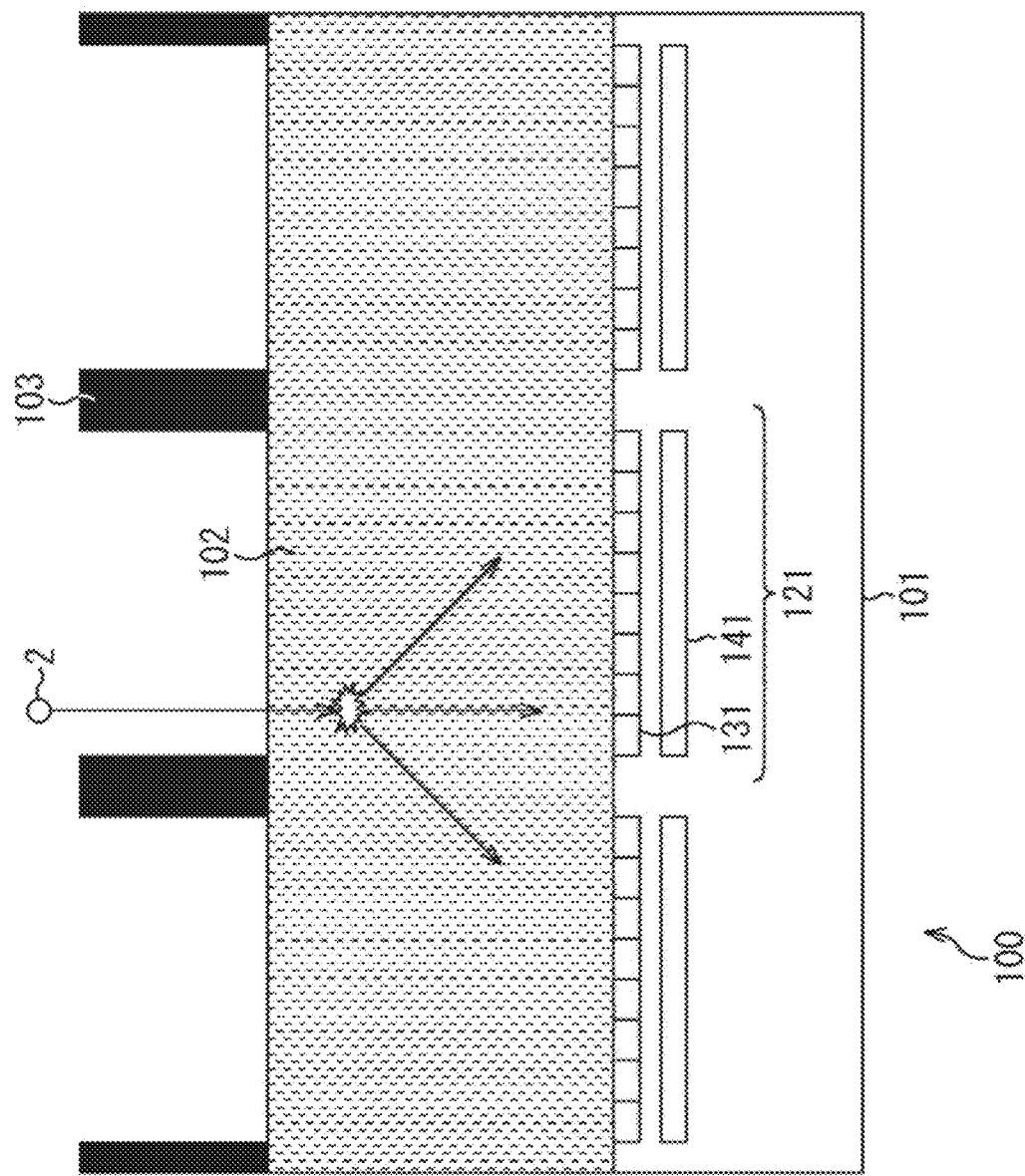
FIG. 16 is a cross-sectional view illustrating an exemplary configuration of an X-ray FPD device to which the present disclosure is applied.

Next, FIG. 16 illustrates an exemplary configuration of an X-ray flat panel detector (FPD) device according to a second embodiment of the present disclosure.

The X-ray FPD device 100 is arranged at a position facing an X-ray irradiation device while interposing a subject (both not illustrated) therebetween. The X-ray FPD device 100 has a photo-detection unit 101 including a silicon semiconductor, a columnar crystal scintillator 102, and a grid 103 to regulate an X-ray incident direction by a lead plate or the like. Note that grid 103 may be formed as needed, and may be omitted.

In the X-ray FPD device 100, X-ray photons 2 having passed through the subject are incident on the scintillator 102. Note that the scintillator 102 of the X-ray FPD device 100 according to the second embodiment is not divided per pixel, unlike the first embodiment.

Therefore, photons of the scintillation light generated in response to incidence of the X-ray photons 2 reach and are incident on a plurality of pixels. Note that the scintillator 102 has a thickness of, for example, 0.6 mm. The emitted X-ray has intensity of, for example, 100 keV.

One pixel 121 in the photo-detection unit 101 has a size of 400 μm square. In one pixel 121, an array is formed by subpixels 131 arranged in 8 rows×8 columns. Each subpixel 131 has a size of, for example, 40 μm square. In an upper layer where the array of the subpixels 131 is formed, a lower layer where a detection unit 141 including an AD conversion circuit is formed in a stacking manner. In other words, a pixel 121 of the photo-detection unit 101 has a configuration similar to a pixel 22 of the first embodiment. Then, an output of the pixel 121 is derived from added-up outputs of the subpixels 131 arranged in 8 rows×8 columns constituting the array.

The photo-detection unit 101 can perform sampling at 33000 Hz, and all of the pixels 121 included in the photo-detection unit 101 simultaneously perform sampling in parallel.

In the X-ray FPD device 100, an X-ray projection image is generated as a moving image in real time by using X-ray counting by energy discrimination. A position of the photo-detection unit 101 where the X-ray photons 2 has been incident is derived every time the X-ray photon 2 is incident on the same, and mapped in two-dimensional X-ray projection data as a counting value for each virtual pixel obtained by virtual division at a pitch of 50 μm, for example, through a process described below.

Figure 17:
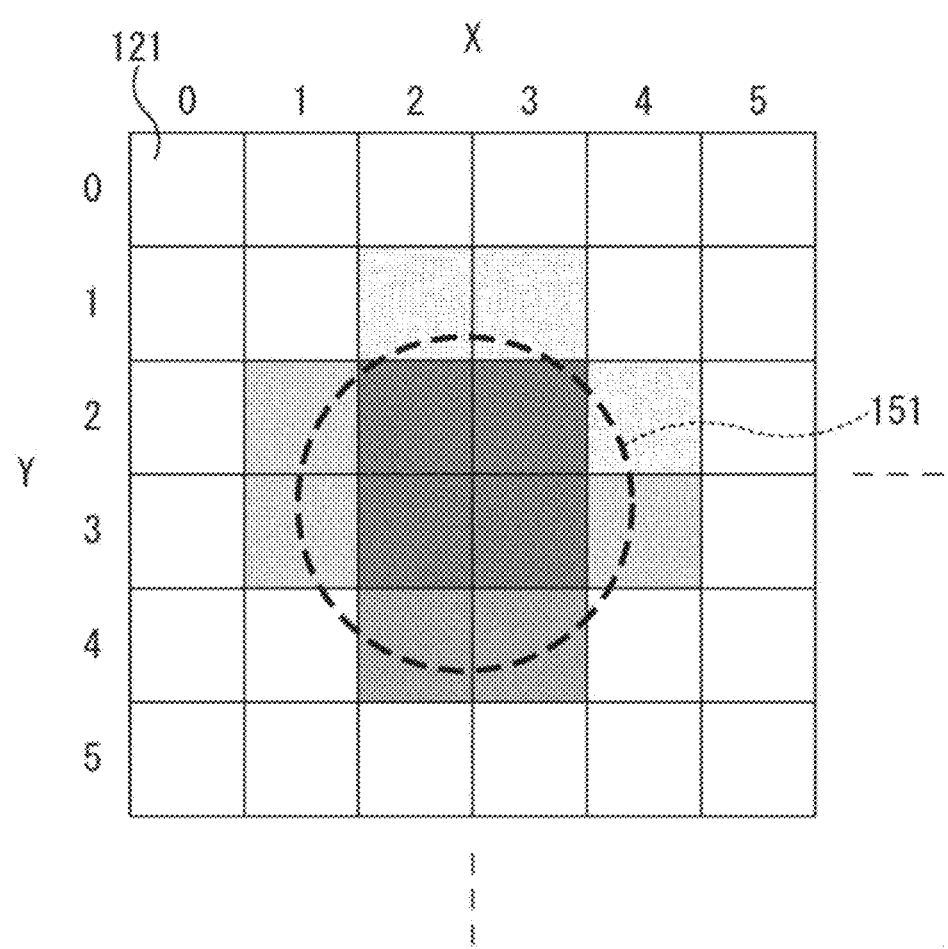
FIG. 17 is a diagram to describe a process of deriving a position where X-ray photons have been incident.

FIG. 17 is a diagram to describe the process of deriving a position in the photo-detection unit 101 where the X-ray photon 2 has been incident.

In the drawings, two-dimensional XY coordinates are illustrated in a manner corresponding to an array of pixels 121 serving as a light receiving surface of the photo-detection unit 101. When one X-ray photon 2 is incident on the photo-detection unit 101 and the scintillator 102 generates scintillation light in response thereto, the scintillation light is diffused in a plane direction while being suppressed by a columnar crystal structure, and is diffused to an entire region 151 of a diameter of about 1.2 mm located around the incidence position, and then the scintillation light is incident on a plurality of pixels 121 in the vicinity of the region 151.

Here, it is considered that the closer to the incidence position, the more increased an incident light amount of the scintillation light on each pixel 121, and the farther to the incidence position, the more decreased the incident light amount. Therefore, an output of each pixel 121 also fluctuates in a manner similar to the incident light amount of scintillation light. A shade of each 121 in the drawing represents an incident light amount.

Accordingly, weighted averaging is performed for outputs of coordinates of pixels 121 located in the vicinity of the incident position, and an incidence coordinate of an X-ray photon 2 is derived by deriving a weight center coordinate thereof. For example, in a case where a pixel output of a coordinate (X, Y) is W (X, Y), a coordinate of an incident position (XC, YC) is derived by a following Formula (1).

[Mathematical Formula 1]

$$X_C = \sum_{x,y}(x \cdot W_{(x,y)}) \Big/ \sum_{x,y} W_{(x,y)} \quad (1)$$

$$Y_C = \sum_{x,y}(y \cdot W_{(x,y)}) \Big/ \sum_{x,y} W_{(x,y)}$$

Since a position accuracy thus derived is higher than that in a case of having the pixel pitch of 400 μm, for example, a virtual pixel obtained by further dividing each pixel 121 into 8×8 at a 50 μm pitch is set, and a derived incidence coordinate is made to correspond to a virtual pixel, and the coordinate is set as a counting value in each virtual pixel, and a two-dimensional X-ray projection image is generated from the results.

Meanwhile, considering spread of the scintillation light, the pixels 121 necessary to derive incidence position of each X-ray photon 2 may be in a range of about 5×5 pixels centering a pixel 121 immediately below the incidence position.

Figure 18:
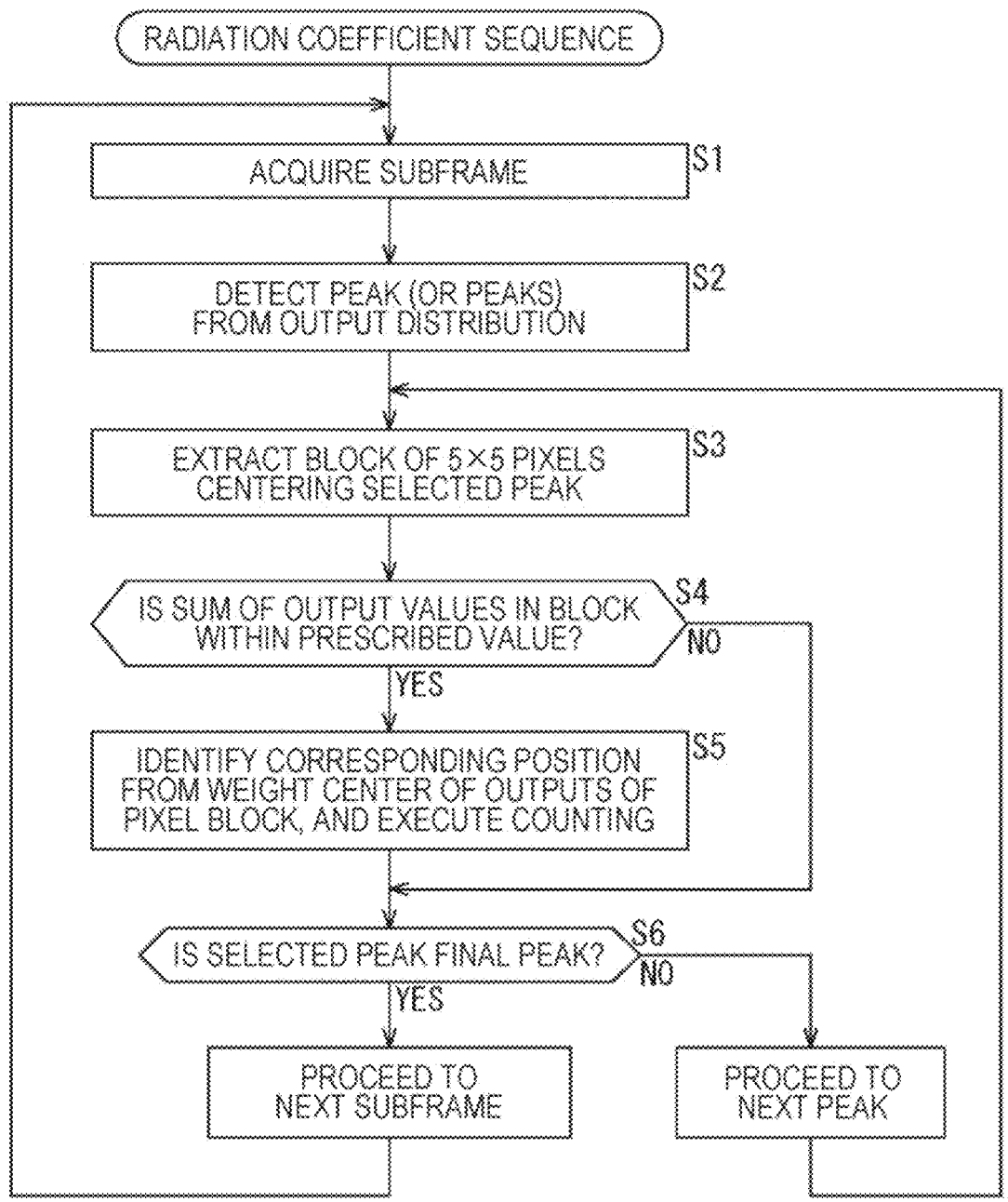
FIG. 18 is a diagram illustrating a sequence to generate an X-ray projection moving image on the basis of two-dimensional X-ray projection data.

FIG. 18 illustrates an exemplary sequence to perform X-ray counting in the X-ray FPD device 100 and generate a real-time X-ray projection moving image on the basis of two-dimensional X-ray projection data.

In step S1, a subframe is acquired. Here, the subframe represents an image obtained by two-dimensionally developing pixel values output in each sampling from a plurality of pixels 121 formed as an array in the photo-detection unit 101. For example, in a case where a sampling rate of a subframe is 33000 Hz, one frame of the X-ray projection moving image of 15 fps is generated from counting results using 2200 subframes.

In step S2, output distribution of the pixels 121 is acquired by the subframe scanning, and positions of a plurality of peaks (coordinates having the darkest shade in FIG. 17) is detected. In step S3, one of the detected peaks is selected, and 5×5 pixels centering the selected peak are extracted.

In step S4, whether or not the sum of pixel values of the extracted 5×5 pixels is within a prescribed range is determined, and in a case where the sum is within the prescribed range, the processing proceeds to step S5 to perform energy discrimination. In step S5, an incidence coordinate of the X-ray photon 2 is derived on the basis of the coordinates of the 5×5 pixels and the pixel values, and further the derived incidence coordinate is made to correspond to a virtual pixel, and +1 counting is performed for each virtual pixel. Meanwhile, in a case where it is determined in step S4 that the sum of the pixel values of 5×5 pixels is not within the prescribed range, energy discrimination is not performed while the sum is deemed as an error, in other words, step S5 is skipped.

In step S6, whether or not a currently selected peak is the final peak in a current subframe (whether or not any other unselected peak remains) is determined, and in a case of determining that the selected peak is the final peak (no unselected peak remains), the processing returns to step S1 in order to acquire a next subframe. In contrast, in a case of determining that the selected peak is not the final peak (unselected peaks remains), the processing returns to step S3 to select a next peak.

Since energy discrimination is executed for each peak detected in each subframe as described above, a subframe image is constructed with one bit virtual pixel. Then, one frame of an X-ray projection moving image of 15 fps is generated by adding corresponding virtual pixels corresponding to 2200 subframe images constructed in the respective 2200 times of sampling.

In this case, gradations of virtual pixels of each frame of the X-ray projection moving image is 11 bits ($\approx \log_2 2200$), but the dynamic range can be largely expanded by applying the first method described with reference to FIG. 14 or the second method described with reference to 15.

Meanwhile, in the case of an X-ray FPD device 100, position correspondence between each pixel 1 and an X-ray projection image is fixed, and therefore, an exposure period may be adjusted by using, for example, a result of a previous frame, or an exposure period may be adjusted for each pixel or for each region. Alternatively, as for a high radiation dose region, integration processing may be performed for data, and a counting image may be corrected by using the integral data.

CONCLUSION

According to the X-ray CT device 10 of the first embodiment and the X-ray FPD device 100 of the second embodiment described above, a sampling rate and spatial resolution can be improved without increasing an exposure dose to a subject.

Note that embodiments of the present disclosure are not limited to the above-described embodiments, and various modifications can be made in a range without departing from the gist of the present disclosure.

The present disclosure can also have the following configuration.

(1)

An X-ray detection device arranged in a manner facing an X-ray irradiation device while interposing a subject and generates X-ray two-dimensional projection data of the subject, and the X-ray detection device including:

a scintillator adapted to generate scintillation light in response to incident X-rays;

a detection unit including a plurality of pixels each generating a pixel signal in response to the scintillation light incident thereon; and an output unit adapted to generate the X-ray two-dimensional projection data by using the pixel signals of the pixels, in which the pixel of the detection unit includes:

a plurality of subpixels adapted to perform photoelectric conversion in response to the scintillation light;

an AD conversion unit adapted to apply AD conversion to outputs of the subpixels; and an adder adapted to generate the pixel signal corresponding to the pixel by adding up outputs of the plurality of subpixels after the AD conversion.

(2)

The X-ray detection device recited in (1) above, in which the AD conversion unit applies AD conversion to an output of the subpixel to obtain a value having a gradation of at least 3 bits or more.

(3)

The X-ray detection device recited in (1) or (2), in which the AD conversion unit is shared by two or more of the subpixels.

(4)

The X-ray detection device recited in any one of (1) to (3) above, in which the subpixel includes:

a photoelectric conversion unit adapted to perform photoelectric conversion in response to the scintillation light, and store electric charge;

a holding unit adapted to hold the electric charge transferred from the photoelectric conversion unit; and a first reset unit adapted to reset the photoelectric conversion unit and the holding unit.

(5)

The X-ray detection device recited in any one of (4) above, in which the subpixel further includes a second reset unit adapted to reset the photoelectric conversion unit not via the holding unit.

(6)

The X-ray detection device recited in (4) or (5) above, in which the photoelectric conversion unit of the subpixel is completely depleted by the first or the second reset unit.

(7)

The X-ray detection device recited in any one of (4) to (6) above, in which a plurality of different exposure periods is set for the subpixels by adjusting timing to reset the photoelectric conversion unit.

(8)

The X-ray detection device recited in (7) above, in which the output unit generates the X-ray two-dimensional projection data by combining the pixel signals based on outputs of the subpixels having different exposure periods (9)

The X-ray detection device recited in any one of (1) to (8) above, in which the output unit performs X-ray counting by discriminating energy while using the pixel signal of the pixel.

(10)

The X-ray detection device recited in any one of (1) to (9) above, in which the output unit further performs, per the pixel, integration of outputs in response to a plurality of times of X-ray irradiation.

(11)

The X-ray detection device recited in (10) above, in which the output unit generates the X-ray two-dimensional projection data by adopting one or a combination of both of: a result of X-ray counting by discriminating energy while using the pixel signal of the pixel; and a result of performing, per the pixel, integration of pixel signals corresponding to the plurality of times of X-ray irradiation.

(12)

A detection method of an X-ray detection device that is arranged in a manner facing an X-ray irradiation device while interposing a subject and generates X-ray two-dimensional projection data of the subject, the X-ray detection device including:

a scintillator adapted to generate scintillation light in response to incident X-rays;

a detection unit including a plurality of pixels each generating a pixel signal in response to the scintillation light incident thereon; and an output unit adapted to generate the X-ray two-dimensional projection data by using the pixel signals of the pixels, the pixel including a plurality of subpixels, the detection method being executed by the pixel, including:

a photoelectric conversion step of performing, by the plurality of subpixels, photoelectric conversion in response to the scintillation light;

an AD conversion step of applying AD conversion to outputs of the subpixels; and an adding-up step of generating the pixel signal corresponding to the pixel by adding up outputs of the plurality of subpixels after the AD conversion.

REFERENCE SIGNS LIST

1 Subject
2 X-ray photon
10 X-ray CT device
11 X-ray irradiation device
12 Detection device
13 Detection panel
21 Semiconductor detection unit
22 Pixel
27 Scintillator
31 Subpixel
61 PD
62 Storage node
63 Transfer Tr
64 Detection node
65 Amplification Tr
66 Selection Tr
67 Reset Tr
68 Power supply line
80 Reset Tr
100 X-ray FPD device
101 Photo-detection unit
102 Scintillator
121 Pixel
131 Subpixel

The invention claimed is:

1. An X-ray detection device comprising:
a scintillator configured to generate scintillation light based on incident X-rays, wherein
the incident X-rays are emitted from an X-ray irradiation device that faces the X-ray detection device, and
a subject is interposed between the X-ray detection device and the X-ray irradiation device;
a detection unit including a plurality of pixels, wherein each pixel of the plurality of pixels is configured to generate a pixel signal based on the scintillation light incident on each pixel of the plurality of pixels; and
an output unit configured to generate X-ray two-dimensional projection data of the subject based on a plurality of pixel signals that corresponds to the plurality of pixels, wherein
the X-ray two-dimensional projection data includes intensity data of the incident X-rays,
each pixel of the plurality of pixels of the detection unit includes:
a plurality of subpixels configured to execute a photoelectric conversion based on the scintillation light;
an analog to digital (AD) conversion unit configured to apply AD conversion to a plurality of outputs of the plurality of subpixels; and
an adder configured to generate the pixel signal corresponding to a pixel of the plurality of pixels based on an addition of the plurality of outputs of the plurality of subpixels after the AD conversion, and
the detection unit is configured to:
calculate a first average value of a plurality of signals output from a subpixel of the plurality of subpixels prior to an exposure period of the scintillation light;
calculate a second average value of a plurality of signals output from the subpixel after the exposure period;
calculate a difference between the first average value and the second average value; and
set the calculated difference as an output of the subpixel.

2. The X-ray detection device according to claim 1, wherein the AD conversion unit is further configured to apply the AD conversion to the output of the subpixel of the plurality of subpixels to obtain a value having a gradation of at least 3 bits or more.

3. The X-ray detection device according to claim 1, wherein the AD conversion unit is shared by two or more subpixels of the plurality of subpixels.

4. The X-ray detection device according to claim 1, wherein the subpixel of the plurality of subpixels includes:
a photoelectric conversion unit configured to:
execute the photoelectric conversion based on the scintillation light; and
store an electric charge based on the photoelectric conversion;
a holding unit configured to hold the electric charge transferred from the photoelectric conversion unit; and
a first reset unit configured to reset the photoelectric conversion unit and the holding unit.

5. The X-ray detection device according to claim 4, wherein the subpixel further includes a second reset unit configured to reset the photoelectric conversion unit not via the holding unit.

6. The X-ray detection device according to claim 5, wherein one of the first reset unit or the second reset unit is further configured to completely deplete the photoelectric conversion unit of the subpixel.

7. The X-ray detection device according to claim 5, wherein a plurality of different exposure periods is set for the plurality of subpixels based on an adjustment in timing to reset the photoelectric conversion unit.

8. The X-ray detection device according to claim 7, wherein
the output unit is further configured to generate the X-ray two-dimensional projection data based on a combination of the plurality of pixel signals,
the combination is based on the plurality of outputs of the plurality of subpixels, and
the plurality of subpixels has the plurality of different exposure periods.

9. The X-ray detection device according to claim 1, wherein the output unit is further configured to execute X-ray counting based on discrimination of energy while using the pixel signal of the pixel.

10. The X-ray detection device according to claim 1, wherein the output unit is further configured to execute, for each pixel of the plurality of pixels, integration of the plurality of outputs of the plurality of subpixels based on a plurality of times of X-ray irradiation.

11. The X-ray detection device according to claim 1, wherein the output unit is further configured to generate the X-ray two-dimensional projection data based on at least one of:
a result of X-ray counting based on discrimination of enemy while using the pixel signal of the pixel, or
a result of integration of the plurality of pixel signals corresponding to a plurality of times of X-ray irradiation.

12. A detection method of an X-ray detection device, the detection method comprising:
executing, by a plurality of subpixels of a pixel, photoelectric conversion based on a scintillation light, wherein
the scintillation light is generated based on incident X-rays,
the incident X-rays are emitted from an X-ray irradiation device that faces the X-ray detection device,
a subject is interposed between the X-ray detection device and the X-ray irradiation device,
the pixel is configured to generate a pixel signal based on the scintillation light incident on the pixel,
X-ray two-dimensional projection data of the subject is generated based on the pixel signal, and
the X-ray two-dimensional projection data includes intensity data of the incident X-rays;
calculating a first average value of a plurality of signals output from a subpixel of the plurality of subpixels prior to an exposure period of the scintillation light;
calculating a second average value of a plurality of signals output from the subpixel after the exposure period;
calculating a difference between the first average value and the second average value;
setting the calculated difference as an output of the subpixel;
applying an analog to digital (AD) conversion to a plurality of outputs of the plurality of subpixels; and
generating the pixel signal based on an addition of the plurality of outputs of the plurality of subpixels after the AD conversion.

* * * * *